US008414887B2

(12) United States Patent
O'Neill et al.

(10) Patent No.: US 8,414,887 B2
(45) Date of Patent: Apr. 9, 2013

(54) METHODS FOR SUPPRESSING TOLL-LIKE RECEPTOR 4 (TLR4) FUNCTION USING TLR14 ANTAGONISTS

(75) Inventors: Luke O'Neill, Dublin (IE); Susan Carpenter, Dublin (IE); Aisling Dunne, Dublin (IE)

(73) Assignee: Opsona Therapeutics Limited, Dublin (IE)

( * ) Notice: Subject to any disclaimer, the term of this patent is extended or adjusted under 35 U.S.C. 154(b) by 0 days.

(21) Appl. No.: 12/446,087

(22) PCT Filed: Oct. 18, 2007

(86) PCT No.: PCT/EP2007/061182
§ 371 (c)(1),
(2), (4) Date: Jul. 10, 2009

(87) PCT Pub. No.: WO2008/046902
PCT Pub. Date: Apr. 24, 2008

(65) Prior Publication Data
US 2010/0330067 A1 Dec. 30, 2010

(30) Foreign Application Priority Data

Oct. 18, 2006 (GB) .................................. 0620705.4

(51) Int. Cl.
*A61K 39/395* (2006.01)
*A61K 38/02* (2006.01)
*C07K 14/435* (2006.01)
*C07K 16/18* (2006.01)

(52) U.S. Cl.
USPC ........ 424/130.1; 514/18.7; 514/1.4; 514/886; 530/389.1; 530/387.9

(58) Field of Classification Search ........................ None
See application file for complete search history.

(56) References Cited

U.S. PATENT DOCUMENTS

| 2009/0054321 A1 | 2/2009 | O'Neill et al. |
| 2009/0123482 A1 | 5/2009 | O'Neill et al. |
| 2010/0297147 A1 | 11/2010 | Seidl et al. |
| 2011/0200605 A1 | 8/2011 | O'Neill et al. |
| 2011/0293635 A1 | 12/2011 | O'Neill et al. |

FOREIGN PATENT DOCUMENTS

| EP | 1734118 A1 | 12/2006 |
| WO | 0021550 A2 | 4/2000 |
| WO | WO/03080640 | * 2/2003 |
| WO | 03025138 A2 | 3/2003 |
| WO | WO/03025138 | * 3/2003 |
| WO | 03035833 A2 | 5/2003 |
| WO | 03/080640 A1 | 10/2003 |
| WO | 2004048938 A2 | 6/2004 |
| WO | 2005065015 A2 | 7/2005 |
| WO | 2006033481 A1 | 3/2006 |
| WO | 2006106492 A2 | 10/2006 |
| WO | WO-2006/111946 | 10/2006 |
| WO | 2007001332 A2 | 1/2007 |
| WO | 2007066313 A2 | 6/2007 |
| WO | 2008046902 A2 | 4/2008 |
| WO | WO-2008/048670 | 4/2008 |
| WO | 2010031801 A2 | 3/2010 |

OTHER PUBLICATIONS

Verbon et al., The Journal of Immunology, 2001, vol. 166, pp. 3599-3605.*
Chilman-Blair et al., E-5564 treatment of septic shock TLR4 (LPS) receptor antagonist. *Drugs of the Future*. 28: 633-9 (2003).
Furusako et al., Protection of mice from LPS-induced shock by CD14 antisense oligonucleotide. *Acta Medica Okayama* 55: 105-15 (2001).
Hawkins et al., Inhibition of endotoxin response by synthetic TLR4 antagonists. *Curr. Topics Med. Chem.* 4: 1147-71 (2004).
Haziot et al., Recombinant soluble CD14 inhibits LPS-induced tumor necrosis factor-alpha production by cells in whole blood. *J Immunol.* 152: 5868-76 (1994).
Leturcq Didier et al., Antibodies against CD14 protect primates from endotoxin-induced shock. *J. Clin. Invest.* 98: 1533-8 (1996).
Mullarkey et al., Inhibition of endotoxin response by E5567, a novel toll like receptor 4 directed endotoxin antagonist. *J. Pharmacol. Exper. Ther.* 304: 1093-1102 (2003).
Rhee et al., Toll-like receptors 2 and 4 activate STAT1 serine phosphorylation by distinct mechanisms in macrophages. *J. Biol. Chem.* 278: 22506-12 (2003).
Roach et al., The evolution of vertebrate toll-like receptors. *Proc. Natl. Acad. Sci. USA*. 102: 9577-82 (2005).
Carpenter et al., "TRIL, a Functional Component of the TLR4 Signaling Complex, Highly Expressed in Brain1," J. Immunol. (2009) 183:3989-3995.
Poltorak et al., "Defective LPS signaling in C3H/HeJ and C57BL/10ScCr mice: mutations in Tlr4 gene," Science (1998) 282(5396):2085-2088.
Qureshi et al., "Endotoxin-tolerant Mice Have Mutations in Toll-Like Receptor 4 (Tlr4)," J. Exp. Med. (1999) 189(4):615-625.
International Search Report and Written Opinion, International Application No. PCT/EP2007/061182, date of mailing Jun. 16, 2008 and Apr. 18, 2009, respectively.
Bsibsi, M., et al. "Broad Expression of Toll-Like Receptors in the Human Central Nervous System," J. Neuropathology and Experimental Neurology, 61(11), pp. 1013-1021, Nov. 2002.
Kielian, T., "Toll-Like Receptors in Central Nervous System Glial Inflammation and Homeostasis," J. of Neuroscience Research, 83:711-730 (2006).
Rolls, et al., "Toll-like Receptors Modulate Adult Hippocampal Neurogenesis," Nat. Cell Biol., 9(9):1081-8 (2007).
Choi, et al., "Modulation of the Purinergic P2X7 Recptor Attenuates Lipopolysaccharide-Mediated Microglial Activation and Neuronal Damage in Inflamed Brain," J. Neuroscience, 27(18):4957-68 (2007).

(Continued)

*Primary Examiner* — Bridget E Bunner
*Assistant Examiner* — Fozia Hamud
(74) *Attorney, Agent, or Firm* — Lando & Anastasi, LLP

(57) ABSTRACT

The present invention relates to compositions and methods for use in the treatment of conditions such as septicaemia and septic shock. The invention further provides compositions and methods for the suppression Toll-like Receptor 4 mediated activation of the immune system. The invention further provides screening assays to identify compounds which have utility in the foregoing compositions and methods.

15 Claims, 14 Drawing Sheets

OTHER PUBLICATIONS

Cao, et al., "Reduced Cerebral Ischemia-Reperfusion Injury in Toll-like Receptor 4 Deficient Mice," BBRC 353:509-514 (2007).

Caso, et al., "Toll-like Receptor 4 is Involved in Brain Damage and Inflammation After Experimental Stroke," Circulation 115(12):1599-1608 (2007).

Jin, J-J, et al., "Toll-like Receptor 4-Dependent Upregulation of Cytokines in a Transgenic Mouse Model of Alzheimer's Disease," Journal of Neuroinflammation, 5(23):1-10 (2008).

Tahara, K., et al., "Role of Toll-like Receptor Signalling in Ab Uptake and Clearance," Brain, 129:3006-3019 (2006).

Arai, H., et al., "Neurotoxic Effects of Kipopolysaccharide on Nigral Dopaminergic Neurons are Mediated by Microglial Activation, Interleukin-1b, and Expression of Caspase-11 in Mice*," The Journal of Biological Chemistry, 279(49):51647-51653 (2004).

Dalrymple, A., et al., "Proteomic Profiling of Plasma in Huntington's Disease Reveals Neuroinflammatory Activation and Biomarker Candidates," Journal of Proteome Research, 6:2833-2840 (2007).

Kang, J. and Serge, R., "MyD88-Deficient Bone Marrow Cells Accelerate Onset and Reduce Survival in a Mouse Model of Amyotrophic Lateral Sclerosis," The Journal of Cell Biology, 179(6):1219-1230 (2007).

Kigerl, K.A., et al., "Toll-like Receptor (TLR)-2 and TLR-4 Regulate Inflammation, Gliosis, and Myelin Sparing After Spinal Cord Injury," Journal of Neurochemistry, 102:37-50 (2007).

Waldner, H., et al., "Activation of Antigen-Presenting Cells by Microbial Products Breaks Self Tolerance and Induces Autoimmune Disease," The Journal of Clinical Investigation, 113(7):990-997 (Apr. 2004).

Tang, S-C., et al., "Pivotal Role for Neuronal Toll-like Receptors in Ischemic Brain Injury and Functional Deficits," PNAS, 104(34):13798-13803 (Aug. 2007).

International Search Report from International Application No. PCT/IE2006/000037 dated Oct. 6, 2006.

Written Opinion from International Application No. PCT/IE2006/000037 dated Oct. 18, 2007.

Axtelle et al., "IC14, CD14 specific monoclonal antibody, is a potential treatment for patients with severe sepsis," J. Endotoxin Res. (2001) 7(4):310-314.

Huang, Q., et al., "Increased Macrophage Activation Mediated Through Toll-like Receptors in Rheumatoid Arthritis," Arthritis & Rheumatism, 56(7):2192-2201 (2007).

Abdollahi-Roodsaz, S., et al., "Inhibition of Toll-like Receptor 4 Breaks the Inflammatory Loop in Autoimmune Destructive Arthritis," Arthritis & Rheumatism, 56(9):2957-2967 (2007).

International Search Report in International Application No. PCT/EP2009/062033 mailed Apr. 6, 2010.

Written Opinion in International Application No. PCT/EP2009/062033 mailed Mar. 16, 2011.

Written Opinion in International Application No. PCT/US2007/022256 mailed Apr. 18, 2009.

Adachi, O., et al. "Targeted Disruption of the MyD88 Gene Results in Loss of IL-1 and IL-18-Mediated Function," Immunity, 9:143-150 (1998).

Ai, et al., "SULF1 and SULF2 regulate heparan sulfate-mediated GDNF Signaling for Esophageal Innervation," Development, 134:3327-3338 (2007).

Barton, et al., "Structure and Axon Outgrowth Inhibitor Binding of the Nogo-66 Receptor and Related Proteins," EMBO, 22:3291-3302 (2003).

Blanco, A., et al., "Involvement of Tlr4/Type I IL-1 Receptor Signalling in the Induction of Inflammatory Mediators and Cell Death Induced by Ethanol FN Cultured Astrocytes," The Journal of Immunology, 175(10):6893-6899 (2005).

Bsibsi, et al., "Identification of Soluble CD14 as an Endogenous Agonist for Troll-Like Receptor 2 on Human Astrocytes by Genome-Scale Functional Screening of Glial Cell Drived Proteins," GLIA, 55:473-482 (2007).

Carpenter, S., et al., "Recent Insights into the Structure of Toll-Like Receptors and Post-Transitional Modifications of Their Associated Signaling Proteins," Biochem., J., 442:1-10 (2009).

Dunne, A., et al., "Minireview: Adaptor Usage and Toll-Like Receptor Signalling Specificity," FEBS Letters, 579:3330-3335 (2005).

Fitzgerald, K.A., et al., "Mal (MyD88-adapter-like) is Required for Toll-Like Receptor-4 Signal Transduction," Nature, 413:78-83 (2001).

Fournier, et al., "Identification of a Receptor Mediating Nogo-66 Inhibition of Axonal Regeneration," Nature, 409:341-346 (2001).

Glezer, et al., "Neuroprotective Role of the Innate Immune System by Microglia," Neuroscience, 147:867-883 (2007).

Hemmi, H., et al., "A Toll-like Receptor Recognizes Bacterial DNA," Nature, 408:740-745 (2000).

Hemmi, H., et al., "Small Anti-Viral Compounds Active Immune Cells via the TLR7 MyD88-dependent Signalling Pathway," Nature Immunol., 3:196-200 (2002).

Hennigan, et al., "Lipopolysaccharide Impairs Long-Term Potentiation and Recognition Memory and Increases p75NTR Expression in teh Rat Dentate Gyrus," Brain Research, 1130:158-166 (2007).

Horng, T., et al., "The Adaptor Molecule TIRAP Provides Signalling Specificity for Toll-like Receptors," Nature 420:329-333 (2002).

Horng, T., et al., "TIRAP: An Adapter Molecule in the Toll Signaling Pathway," Nature Immunol., 2:835-841 (2001).

Ishikawa, K., et al., "Prediction of the Coding Sequences of Unidentified Human Genes. X. The Complete Sequences of 100 New cDNA Clones from Brain which Can Code for Large Proteins in Vitro," DNA Research, 5:169-176 (1998).

Kaisho, T., et al., "Endotoxin-Induced Maturation of MyD88-Deficient Dendritic Cells," J. Immunol., 166:5688-5694 (2001).

Karnezis et al., "The Neurite Outgrowth Inhibitor Nogo A is Involved in Autoimmune-Mediated Demyelination," Nature Neuroscience, 30(7):736-744 (2004).

Lauren, et al., Two Novel Mammlian Nogo Receptor Homologs Differentially Expressed in teh Central and Peripheral Nervous System, Mol. Cell. Neurosci., 24:581-594 (2003).

Lee, et al., "Nogo Receptor Antagonism Promotes Stroke Recovery by Enhancing Axonal Plasticity," Journal of Neuroscience, 24:6209-6217 (2004).

Lin, L., "Rage on the Toll Road?" Cellular and Molecular Immunology, 3(5):351-358 (2006).

McGregor, et al., "p75(NTR) Gene and Suicide Attempts in Young Adults with a History of Childhood-Onset Mood Disorder," Am. J. Med. Genet. B. Neurophyshiatr. Genet., 144B:696-700 (2007).

Okazaki, N., et al., "Prediction of the Coding Sequences of Mouse Homologues of KIAA Gene: II. The Complete Nucleotide Sequences of 400 Mouse KIAA-Homologous cDNAs Identified by Screening of Terminal Sequences of cDNA Clones Randomly Sampled from Size-Fractionated Libraries," DNA Research, 10(1):35-48 (Feb. 28, 2003).

Oliveira, R., et al., "Expression of 1-33 Toll-Like Receptor 2 on Human Schwann Cell S:A Mechanism of Nerve Damage in Leprosy," Infection and Immunity, 71(3):1427-1433 (2003).

Scumpia, P., et al., "Double-Stranded RNA Signals Antiviral and Inflammatory Programs and Dysfunctional Gluatamate Transport in tlr3-Expressing Astrocytes," GLIA, 52(2):153-162 (2005).

Servant, M.J. et al., "Multiple Signaling Pathways Leading to the Activation of Interferon Regulatory Factor 3," J. Biochem. Pharmacol., 64:985-992 (2002).

Su, A., et al., "Large-Scale Analysis of the Human and Mouse Transcriptomes," PNAS, 99(7):4465-4470 (2002).

Tabeta, K., et al., "Toll-Like Receptors 9 and 3 as Essential Components of Innate Immune Defense Against Mouse Cytomegalovirus Infection," PNAS 101:3516-3521 (2004).

Takeuchi, O., et al., "Cutting Edge: Preferentially the R-Stereoisomer of the Mycoplasmal Lipopeptide Macrophage-Activating Lipopeptide-2 Activates Immune Cells Through a Toll-Like Receptor 2- and MyD88-Dependent Signaling Pathway," J. Immunol., 164:554-557 (2000).

Walmsley and Mir, "Targeting the Nogo-A Signalling Pathway to Promote Recovery Following Acute CNS Injury," Curr. Pharm. Res., 13:2470-2484 (2007).

Yamamoto, M., et al., "Cutting Edge: A Novel Toll/IL-1 Receptor Domain-Containing Adapter that Preferentially Activates the IFN-Beta Promoter in the Toll-like Receptor Signalling," J. Immunol., 169:6668-72 (2002).

Yamomoto, M., et al., "Essential Role for TIRAP in Activation of the Signalling Cascade Shared by TLR2 and TLR4," Nature 420:324-329 (2002).

Yu, et al., "DNA Vaccine Against NgR Promotes Functional Recovery After Spinal Cord Injury in Adult Rats," Brain Research, 1147:66-76 (2007).

Zhang, D., et al., "A Toll-like Receptor that Prevents Infection by Uropathogenic Bacteria," Science, 303:1522-1526 (2004).

International Search Report for PCT/US2007/022256, dated Jun. 27, 2008, 9 pages.

Hayashi, F., et al. "The Innate Immune Response to Bacterial Flagellin is Mediated by Toll-like Receptor 5," Nature, 410:1099-1103 (2001).

* cited by examiner

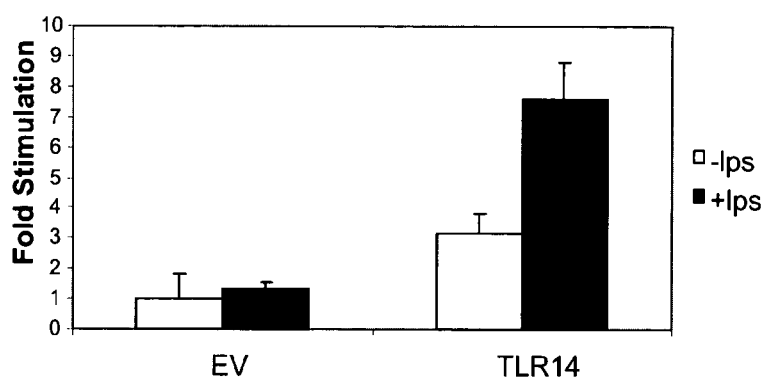
Figure 1 - TLR14 enhances LPS signalling

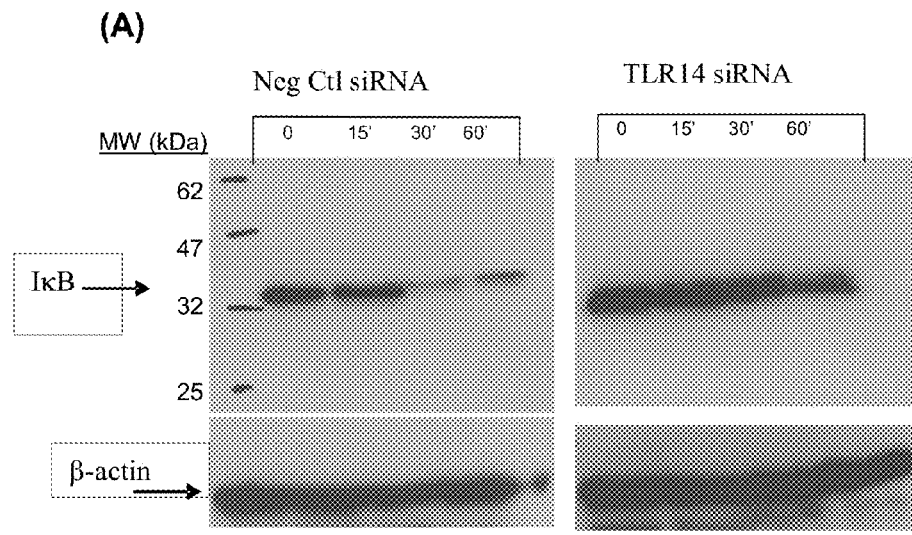
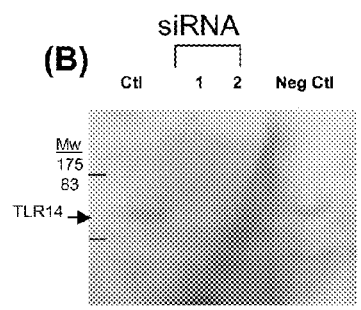
Figure 2 - Knockdown of TLR14 abolishes LPS induced IkB degradation

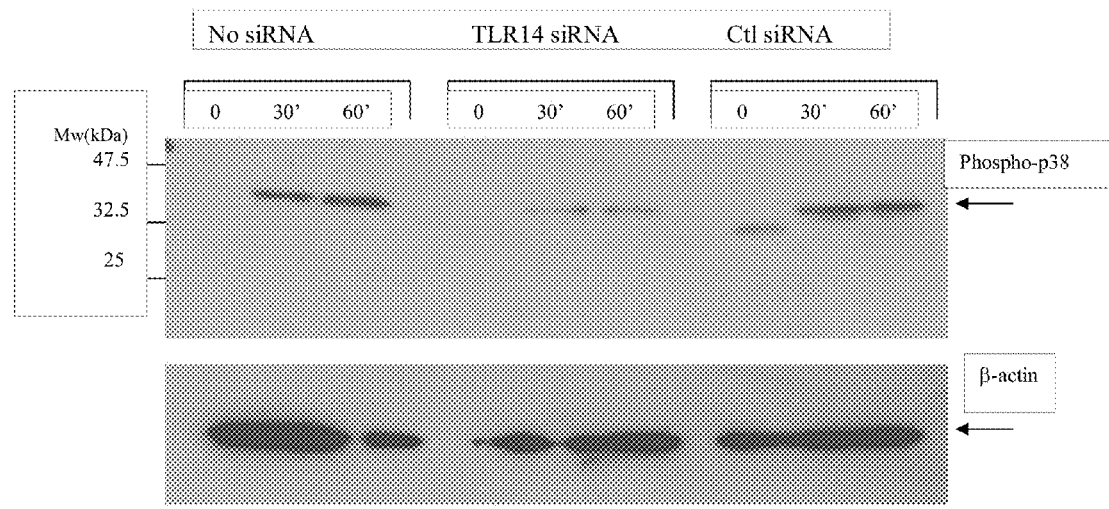
Figure 3 – knockdown of TLR14 abolishes LPS induced p38 phosphorylation

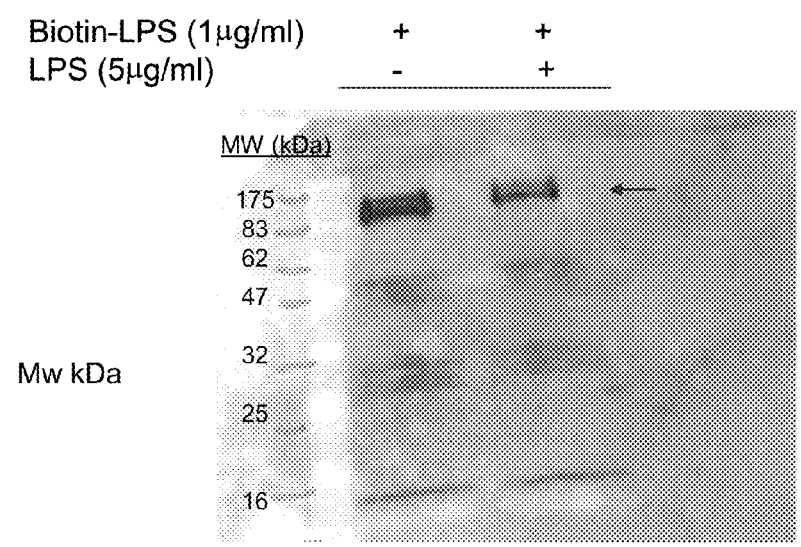
Figure 4(a) - TLR14 binds to LPS.

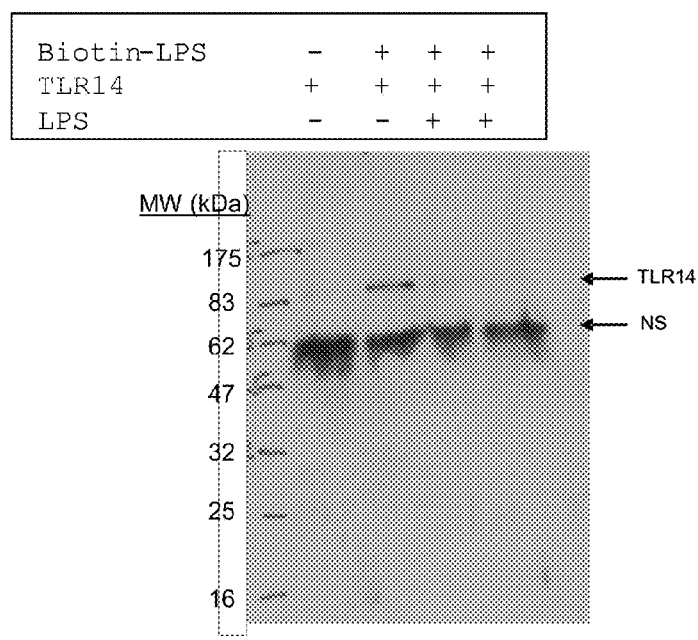
Figure 4(b) – TLR14 binds to LPS

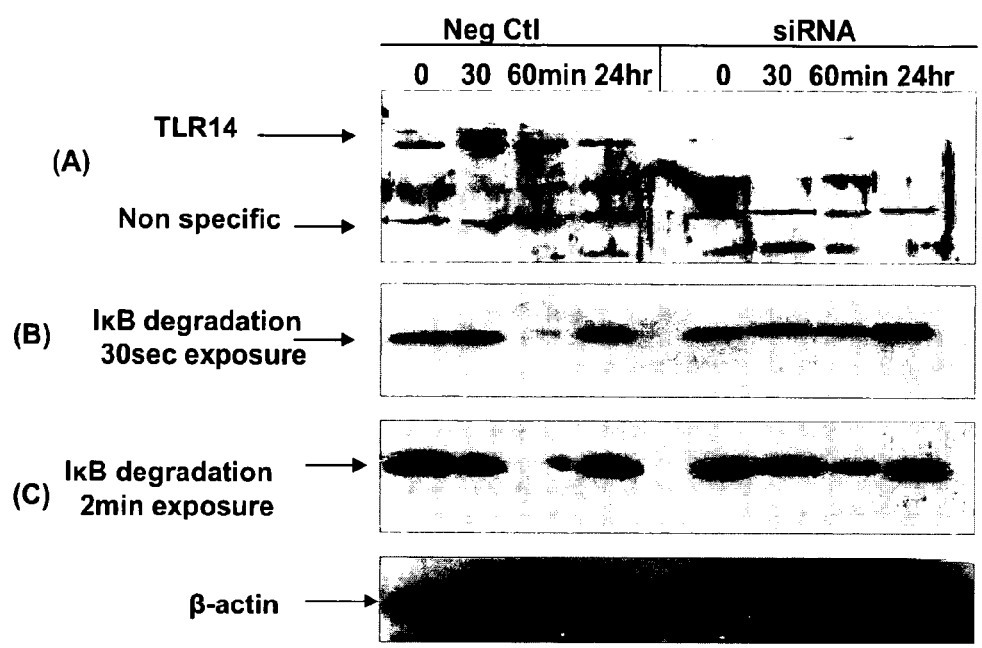
Figure 5: Knockdown of TLR14 marginally inhibits IκB degradation in response to LPS (A) Cytokine release from THP1s, amaxa transfection
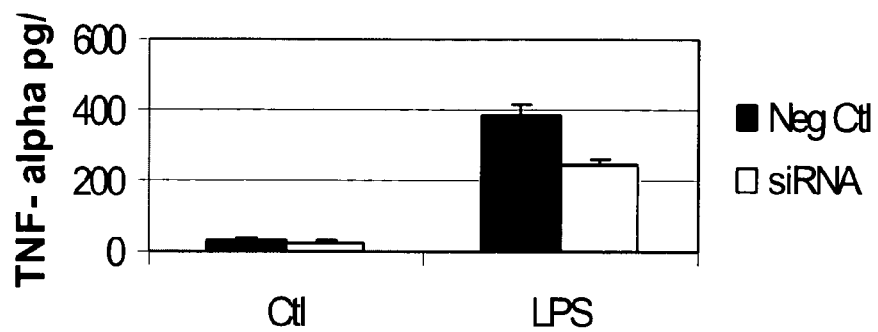
(B) Cytokine release from THP1s using amaxa
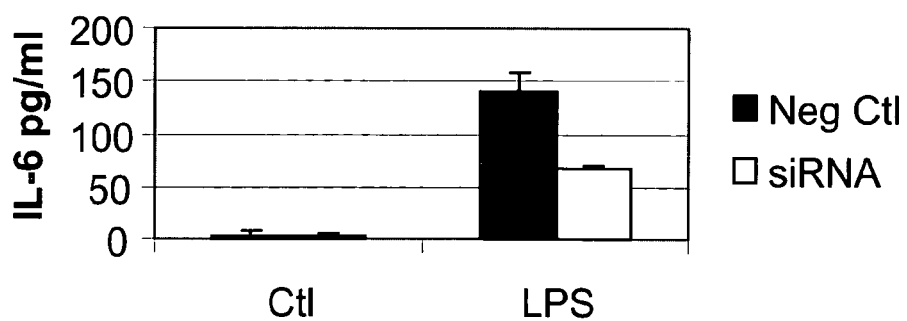
Figure 6: Knockdown of TLR14 causes a decrease in IL-6 (B) and TNF-α (A) cytokine production from THP1 cells

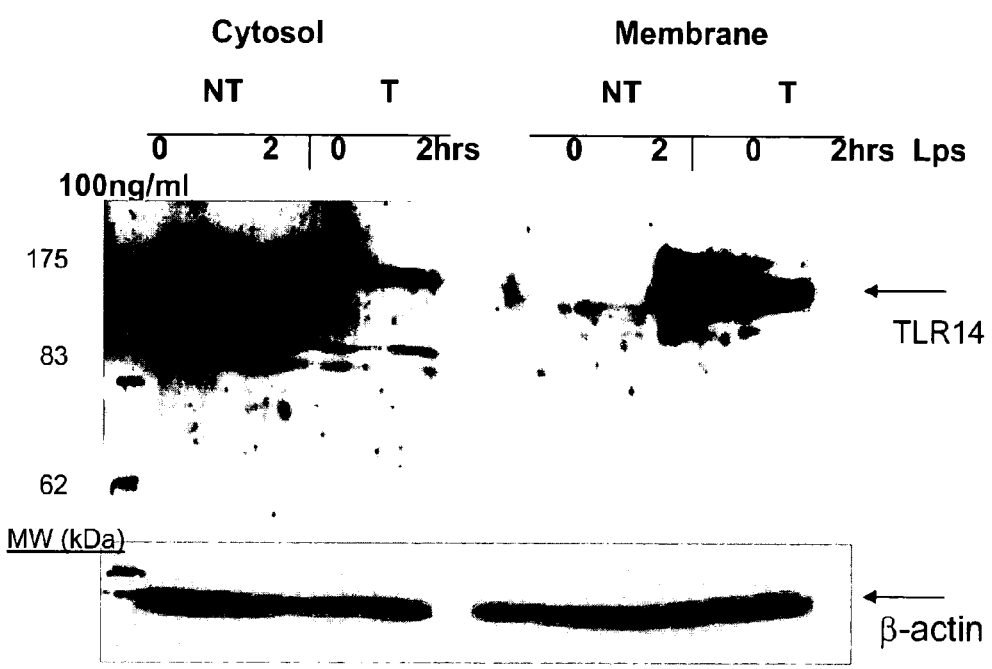
Figure 7 - Over-expressed TLR14 is localized in the membrane

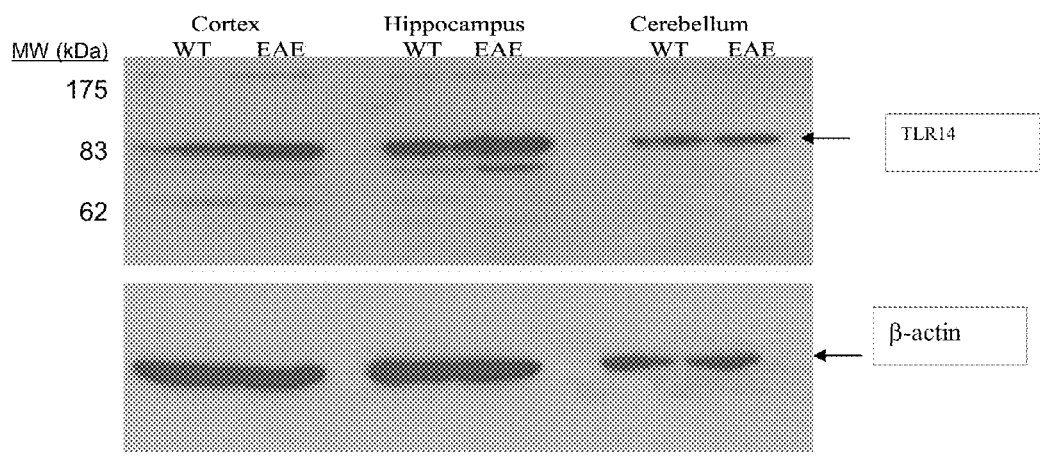
Figure 8: Presence of TLR14 in mice brain

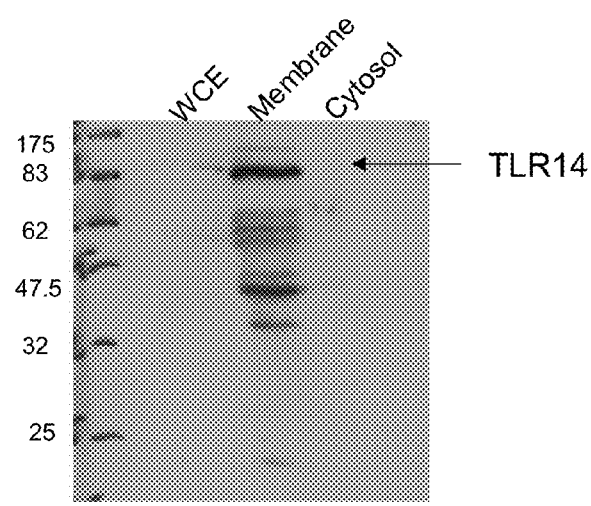
Figure 9 - Localisation of endogenous TLR14 in THP1 cells

MEAARALRLLLVVCGCLALPPLAEPVCPERCDCQHPQHLLCTNRGLRVVPKTS
SLPSPHDVLTYSLGGNFITNITAFDFHRLGQLRRLDLQYNQIRSLHPKTFEKL
SRLEELYLGNNLLQALAPGTLAPLRKLRILYANGNEISRLSRGSFEGLESLVK
LRLDGNALGALPDAVFAPLGNLLYLHLESNRIRFLGKNAFAQLGKLRFLNLSA
NELQPSLRHAATFAPLRSLSSLILSANSLQHLGPRIFQHLPRLGLLSLRGNQL
THLAPEAFWGLEALRELRLEGNRLSQLPTALLEPLHSLEALDLSGNELSALHP
ATFGHLGRLRELSLRNNALSALSGDIFAASPALYRLDLDGNGWTCDCRLRGLK
RWMGDWHSQGRLLTVFVQCRHPPALRGKYLDYLDDQQLQNGSCADPSPSASLT
ADRRRQPLPTAAGEEMTPPAGLAEELPPQPQLQQQGRFLAGVAWDGAARELVG
NRSALRLSRRGPGLQQPSPSVAAAAGPAPQSLDLHKKPQRGRPTRADPALAEP
TPTASPGSAPSPAGDPWQRATKHRLGTEHQERAAQSDGGAGLPPLVSDPCDFN
KFILCNLTVEAVGADSASVRWAVREHRSPRPLGGARFRLLFDRFGQQPKFHRF
VYLPESSDSATLRELRGDTPYLVCVEGVLGGRVCPVAPRDHCAGLVTLPEAGS
RGGVDYQLLTLALLTVNALLVLLALAAWASRWLRRKLRARRKGGAPVHVRHMY
STRRPLRSMGTGVSADFSGFQSHRPRTTVCALSEADLIEFPCDRFMDSAGGGA
GGSLRREDRLLQRFAD

Figure 10 – SEQ ID NO:1 - Amino acid sequence of human Toll-like Receptor 14

```
MEAARALRLLLVVCGCLALPPLAEPVCPERCDCQHPQHLLCTNRGLRVVPKTS
SLPSPHDVLTYSLGGNFITNITAFDFHRLGQLRRLDLQYNQIRSLHPKTFEKL
SRLEELYLGNNLLQALAPGTLAPLRKLRILYANGNEISRLSRGSFEGLESLVK
LRLDGNALGALPDAVFAPLGNLLYLHLESNRIRFLGKNAFAQLGKLRFLNLSA
NELQPSLRHAATFAPLRSLSSLILSANSLQHLGPRIFQHLPRLGLLSLRGNQL
THLAPEAFWGLEALRELRLEGNRLSQLPTALLEPLHSLEALDLSGNELSALHP
ATFGHLGRLRELSLRNNALSALSGDIFAASPALYRLDLDGNGWTCDCRLRGLK
RWMGDWHSQGRLLTVFVQCRHPPALRGKYLDYLDDQQLQNGSCADPSPSASLT
ADRRRQPLPTAAGEEMTPPAGLAEELPPQPQLQQQGRFLAGVAWDGAARELVG
NRSALRLSRRGPGLQQPSPSVAAAAGPAPQSLDLHKKPQRGRPTRADPALAEP
TPTASPGSAPSPAGDPWQRATKHRLGTEHQERAAQSDGGAGLPPLVSDPCDFN
KFILCNLTVEAVGADSASVRWAVREHRSPRPLGGARFRLLFDRFGQQPKFHRF
VYLPESSDSATLRELRGDTPYLVCVEGVLGGRVCPVAPRDHCAGLVTLPEAGS
RGGVDYQL
```

Figure 11 – SEQ ID NO:2 - Amino acid sequence of predicted soluble form of human Toll-like Receptor 14

```
MEGVGAVRFWLVVCGCLAFPPRAESVCPERCDCQHPQHLLCTNRGLRAVPKTS
SLPSPQDVLTYSLGGNFITNITAFDFHRLGQLRRLDLQYNQIRSLHPKTFEKL
SRLEELYLGNNLLQALVPGTLAPLRKLRILYANGNEIGRLSRGSFEGLESLVK
LRLDGNVLGALPDAVFAPLGNLLYLHLESNRIRFLGKNAFSQLGKLRFLNLSA
NELQPSLRHAATFVPLRSLSTLILSANSLQHLGPRVFQHLPRLGLLSLSGNQL
THLAPEAFWGLEALRELRLEGNRLNQLPLTLLEPLHSLEALDLSGNELSALHP
ATFGHQGRLRELSLRDNALSALSGDIFAASPALYRLDLDGNGWTCDCRLRGLK
RWMGNWHSQGRLLTVFVQCRHPPALRGKYLDYLDDQLLQNGSCVDPSPSPTAG
SRQWPLPTSSEEGMTPPAGLSQELPLQPQPQPQQRGRLLPGVAWGGAAKELVG
NRSALRLSRRGPGPHQGPSAAAPGSAPQSLDLHEKPGRGRHTRANLSQTEPTP
TSEPASGTPSARDSWQRAAKQRLASEQQESAVQSVSGVGLPPLVSDPCDFNKF
ILCNLTVEAVSANSASVRWAVREHRSPRPQGGARFRLLFDRFGQQPKFQRFVY
LPERSDSATLHELRGDTPYLVCVEGVLGGRVCPVAPRDHCAGLVTLPEAGGRG
GVDYQLLTLVLLAVNALLVLLALAAWGSRWLRRKLRARRKGGAPVHVRHMYST
RRPLRSMGTGVSADFSGFQSHRPRTTVCALSEADLIEFPCDRFMDSTGGGTSG
SLRREDHLLQRFAD
```

Figure 12 – SEQ ID NO:3 - Amino acid sequence of murine Toll-like Receptor 14

```
MELNFYKIPDNLPFSTKNLDLSFNPLRHLGSYSFFSFPELQVLDLSRCEI
QTIEDGAYQSLSHLSTLILTGNPIQSLALGAFSGLSSLQKLVAVETNLAS
LENFPIGHLKTLKELNVAHNLIQSFKLPEYFSNLTNLEHLDLSSNKIQSI
YCTDLRVLHQMPLLNLSLDLSLNPMNFIQPGAFKEIRLHKLTLRNNFDSL
NVMKTCIQGLAGLEVHRLVLGEFRNEGNLEKFDKSALEGLCNLTIEEFRL
AYLDYYLDDIIDLFNCLTNVSSFSLVSVTIERVKDFSYNFGWQHLELVNC
KFGQFPTLKLKSLKRLTFTSNKGGNAFSEVDLPSLEFLDLSRNGLSFKGC
CSQSDFGTTSLKYLDLSFNGVITMSSNFLGLEQLEHLDFQHSNLKQMSEF
SVFLSLRNLIYLDISHTHTRVAFNGIFNGLSSLEVLKMAGNSFQENFLPD
IFTELRNLTFLDLSQCQLEQLSPTAFNSLSSLQVLNMSHNNFFSLDTFPY
KCLNSLQVLDYSLNHIMTSKKQELQHFPSSLAFLNLTQNDFACTCEHQSF
LQWIKDQRQLLVEVERMECATPSDKQGMPVLSLNITCQMNKTIIGVSVLS
VLVVSVVAVLVYKFYFHLMLLAGCIKYGRGENIYDAFVIYSSQDEDWVRN
ELVKNLEEGVPPFQLCLHYRDFIPGVAIAANIIHEGFHKSRKVIVVVSQH
FIQSRWCIFEYEIAQTWQFLSSRAGIIFIVLQKVEKTLLRQQVELYRLLS
RNTYLEWEDSVLGRHIFWRRLRKALLDGKSWNPEGTVGTGCNWQEATSI
```

Figure 13 – SEQ ID NO:4 - Amino acid sequence of human Toll-like Receptor 4

SEQUENCE LISTING

```
<160> NUMBER OF SEQ ID NOS: 4

<210> SEQ ID NO 1
<211> LENGTH: 811
<212> TYPE: PRT
<213> ORGANISM: Homo sapiens

<400> SEQUENCE: 1

Met Glu Ala Ala Arg Ala Leu Arg Leu Leu Leu Val Val Cys Gly Cys
1               5                   10                  15

Leu Ala Leu Pro Pro Leu Ala Glu Pro Val Cys Pro Glu Arg Cys Asp
            20                  25                  30

Cys Gln His Pro Gln His Leu Leu Cys Thr Asn Arg Gly Leu Arg Val
        35                  40                  45

Val Pro Lys Thr Ser Ser Leu Pro Ser Pro His Asp Val Leu Thr Tyr
    50                  55                  60

Ser Leu Gly Gly Asn Phe Ile Thr Asn Ile Thr Ala Phe Asp Phe His
65                  70                  75                  80

Arg Leu Gly Gln Leu Arg Arg Leu Asp Leu Gln Tyr Asn Gln Ile Arg
                85                  90                  95

Ser Leu His Pro Lys Thr Phe Glu Lys Leu Ser Arg Leu Glu Glu Leu
            100                 105                 110

Tyr Leu Gly Asn Asn Leu Leu Gln Ala Leu Ala Pro Gly Thr Leu Ala
        115                 120                 125

Pro Leu Arg Lys Leu Arg Ile Leu Tyr Ala Asn Gly Asn Glu Ile Ser
    130                 135                 140

Arg Leu Ser Arg Gly Ser Phe Glu Gly Leu Glu Ser Leu Val Lys Leu
145                 150                 155                 160

Arg Leu Asp Gly Asn Ala Leu Gly Ala Leu Pro Asp Ala Val Phe Ala
                165                 170                 175

Pro Leu Gly Asn Leu Leu Tyr Leu His Leu Glu Ser Asn Arg Ile Arg
            180                 185                 190
```

```
Phe Leu Gly Lys Asn Ala Phe Ala Gln Leu Gly Lys Leu Arg Phe Leu
            195                 200                 205

Asn Leu Ser Ala Asn Glu Leu Gln Pro Ser Leu Arg His Ala Ala Thr
        210                 215                 220

Phe Ala Pro Leu Arg Ser Leu Ser Ser Leu Ile Leu Ser Ala Asn Ser
225                 230                 235                 240

Leu Gln His Leu Gly Pro Arg Ile Phe Gln His Leu Pro Arg Leu Gly
                245                 250                 255

Leu Leu Ser Leu Arg Gly Asn Gln Leu Thr His Leu Ala Pro Glu Ala
            260                 265                 270

Phe Trp Gly Leu Glu Ala Leu Arg Glu Leu Arg Leu Glu Gly Asn Arg
        275                 280                 285

Leu Ser Gln Leu Pro Thr Ala Leu Leu Glu Pro Leu His Ser Leu Glu
    290                 295                 300

Ala Leu Asp Leu Ser Gly Asn Glu Leu Ser Ala Leu His Pro Ala Thr
305                 310                 315                 320

Phe Gly His Leu Gly Arg Leu Arg Glu Leu Ser Leu Arg Asn Asn Ala
                325                 330                 335

Leu Ser Ala Leu Ser Gly Asp Ile Phe Ala Ala Ser Pro Ala Leu Tyr
            340                 345                 350

Arg Leu Asp Leu Asp Gly Asn Gly Trp Thr Cys Asp Cys Arg Leu Arg
        355                 360                 365

Gly Leu Lys Arg Trp Met Gly Asp Trp His Ser Gln Gly Arg Leu Leu
    370                 375                 380

Thr Val Phe Val Gln Cys Arg His Pro Ala Leu Arg Gly Lys Tyr
385                 390                 395                 400

Leu Asp Tyr Leu Asp Asp Gln Gln Leu Gln Asn Gly Ser Cys Ala Asp
                405                 410                 415

Pro Ser Pro Ser Ala Ser Leu Thr Ala Asp Arg Arg Gln Pro Leu
            420                 425                 430

Pro Thr Ala Ala Gly Glu Glu Met Thr Pro Pro Ala Gly Leu Ala Glu
        435                 440                 445

Glu Leu Pro Pro Gln Pro Gln Leu Gln Gln Gly Arg Phe Leu Ala
    450                 455                 460

Gly Val Ala Trp Asp Gly Ala Ala Arg Glu Leu Val Gly Asn Arg Ser
465                 470                 475                 480

Ala Leu Arg Leu Ser Arg Arg Gly Pro Gly Leu Gln Gln Pro Ser Pro
                485                 490                 495

Ser Val Ala Ala Ala Gly Pro Ala Pro Gln Ser Leu Asp Leu His
            500                 505                 510

Lys Lys Pro Gln Arg Gly Arg Pro Thr Arg Ala Asp Pro Ala Leu Ala
        515                 520                 525

Glu Pro Thr Pro Thr Ala Ser Pro Gly Ser Ala Pro Ser Pro Ala Gly
    530                 535                 540

Asp Pro Trp Gln Arg Ala Thr Lys His Arg Leu Gly Thr Glu His Gln
545                 550                 555                 560

Glu Arg Ala Ala Gln Ser Asp Gly Gly Ala Gly Leu Pro Pro Leu Val
                565                 570                 575

Ser Asp Pro Cys Asp Phe Asn Lys Phe Ile Leu Cys Asn Leu Thr Val
            580                 585                 590

Glu Ala Val Gly Ala Asp Ser Ala Ser Val Arg Trp Ala Val Arg Glu
        595                 600                 605

His Arg Ser Pro Arg Pro Leu Gly Gly Ala Arg Phe Arg Leu Leu Phe
    610                 615                 620
```

-continued

```
Asp Arg Phe Gly Gln Gln Pro Lys Phe His Arg Phe Val Tyr Leu Pro
625                 630                 635                 640

Glu Ser Ser Asp Ser Ala Thr Leu Arg Glu Leu Arg Gly Asp Thr Pro
            645                 650                 655

Tyr Leu Val Cys Val Glu Gly Val Leu Gly Arg Val Cys Pro Val
        660                 665                 670

Ala Pro Arg Asp His Cys Ala Gly Leu Val Thr Leu Pro Glu Ala Gly
        675                 680                 685

Ser Arg Gly Gly Val Asp Tyr Gln Leu Leu Thr Leu Ala Leu Leu Thr
690                 695                 700

Val Asn Ala Leu Leu Val Leu Leu Ala Leu Ala Ala Trp Ala Ser Arg
705                 710                 715                 720

Trp Leu Arg Arg Lys Leu Arg Ala Arg Lys Gly Gly Ala Pro Val
            725                 730                 735

His Val Arg His Met Tyr Ser Thr Arg Arg Pro Leu Arg Ser Met Gly
            740                 745                 750

Thr Gly Val Ser Ala Asp Phe Ser Gly Phe Gln Ser His Arg Pro Arg
            755                 760                 765

Thr Thr Val Cys Ala Leu Ser Glu Ala Asp Leu Ile Glu Phe Pro Cys
            770                 775                 780

Asp Arg Phe Met Asp Ser Ala Gly Gly Ala Gly Gly Ser Leu Arg
785                 790                 795                 800

Arg Glu Asp Arg Leu Leu Gln Arg Phe Ala Asp
                805                 810

<210> SEQ ID NO 2
<211> LENGTH: 697
<212> TYPE: PRT
<213> ORGANISM: Homo sapiens

<400> SEQUENCE: 2

Met Glu Ala Ala Arg Ala Leu Arg Leu Leu Val Val Cys Gly Cys
1               5                   10                  15

Leu Ala Leu Pro Pro Leu Ala Glu Pro Val Cys Pro Glu Arg Cys Asp
            20                  25                  30

Cys Gln His Pro Gln His Leu Leu Cys Thr Asn Arg Gly Leu Arg Val
        35                  40                  45

Val Pro Lys Thr Ser Ser Leu Pro Ser Pro His Asp Val Leu Thr Tyr
    50                  55                  60

Ser Leu Gly Gly Asn Phe Ile Thr Asn Ile Thr Ala Phe Asp Phe His
65                  70                  75                  80

Arg Leu Gly Gln Leu Arg Arg Leu Asp Leu Gln Tyr Asn Gln Ile Arg
                85                  90                  95

Ser Leu His Pro Lys Thr Phe Glu Lys Leu Ser Arg Leu Glu Glu Leu
            100                 105                 110

Tyr Leu Gly Asn Asn Leu Leu Gln Ala Leu Ala Pro Gly Thr Leu Ala
        115                 120                 125

Pro Leu Arg Lys Leu Arg Ile Leu Tyr Ala Asn Gly Asn Glu Ile Ser
    130                 135                 140

Arg Leu Ser Arg Gly Ser Phe Glu Gly Leu Glu Ser Leu Val Lys Leu
145                 150                 155                 160

Arg Leu Asp Gly Asn Ala Leu Gly Ala Leu Pro Asp Ala Val Phe Ala
                165                 170                 175

Pro Leu Gly Asn Leu Leu Tyr Leu His Leu Glu Ser Asn Arg Ile Arg
            180                 185                 190
```

```
Phe Leu Gly Lys Asn Ala Phe Ala Gln Leu Gly Lys Leu Arg Phe Leu
            195                 200                 205

Asn Leu Ser Ala Asn Glu Leu Gln Pro Ser Leu Arg His Ala Ala Thr
            210                 215                 220

Phe Ala Pro Leu Arg Ser Leu Ser Ser Leu Ile Leu Ser Ala Asn Ser
225                 230                 235                 240

Leu Gln His Leu Gly Pro Arg Ile Phe Gln His Leu Pro Arg Leu Gly
            245                 250                 255

Leu Leu Ser Leu Arg Gly Asn Gln Leu Thr His Leu Ala Pro Glu Ala
            260                 265                 270

Phe Trp Gly Leu Glu Ala Leu Arg Glu Leu Arg Leu Glu Gly Asn Arg
            275                 280                 285

Leu Ser Gln Leu Pro Thr Ala Leu Leu Glu Pro Leu His Ser Leu Glu
            290                 295                 300

Ala Leu Asp Leu Ser Gly Asn Glu Leu Ser Ala Leu His Pro Ala Thr
305                 310                 315                 320

Phe Gly His Leu Gly Arg Leu Arg Glu Leu Ser Leu Arg Asn Asn Ala
            325                 330                 335

Leu Ser Ala Leu Ser Gly Asp Ile Phe Ala Ala Ser Pro Ala Leu Tyr
            340                 345                 350

Arg Leu Asp Leu Asp Gly Asn Gly Trp Thr Cys Asp Cys Arg Leu Arg
            355                 360                 365

Gly Leu Lys Arg Trp Met Gly Asp Trp His Ser Gln Gly Arg Leu Leu
            370                 375                 380

Thr Val Phe Val Gln Cys Arg His Pro Pro Ala Leu Arg Gly Lys Tyr
385                 390                 395                 400

Leu Asp Tyr Leu Asp Asp Gln Gln Leu Gln Asn Gly Ser Cys Ala Asp
            405                 410                 415

Pro Ser Pro Ser Ala Ser Leu Thr Ala Asp Arg Arg Gln Pro Leu
            420                 425                 430

Pro Thr Ala Ala Gly Glu Glu Met Thr Pro Pro Ala Gly Leu Ala Glu
            435                 440                 445

Glu Leu Pro Pro Gln Pro Gln Leu Gln Gln Gln Gly Arg Phe Leu Ala
            450                 455                 460

Gly Val Ala Trp Asp Gly Ala Ala Arg Glu Leu Val Gly Asn Arg Ser
465                 470                 475                 480

Ala Leu Arg Leu Ser Arg Arg Gly Pro Gly Leu Gln Gln Pro Ser Pro
            485                 490                 495

Ser Val Ala Ala Ala Ala Gly Pro Ala Pro Gln Ser Leu Asp Leu His
            500                 505                 510

Lys Lys Pro Gln Arg Gly Arg Pro Thr Arg Ala Asp Pro Ala Leu Ala
            515                 520                 525

Glu Pro Thr Pro Thr Ala Ser Pro Gly Ser Ala Pro Ser Pro Ala Gly
            530                 535                 540

Asp Pro Trp Gln Arg Ala Thr Lys His Arg Leu Gly Thr Glu His Gln
545                 550                 555                 560

Glu Arg Ala Ala Gln Ser Asp Gly Gly Ala Gly Leu Pro Pro Leu Val
            565                 570                 575

Ser Asp Pro Cys Asp Phe Asn Lys Phe Ile Leu Cys Asn Leu Thr Val
            580                 585                 590

Glu Ala Val Gly Ala Asp Ser Ala Ser Val Arg Trp Ala Val Arg Glu
            595                 600                 605

His Arg Ser Pro Arg Pro Leu Gly Gly Ala Arg Phe Arg Leu Leu Phe
```

-continued

```
                610                 615                 620
Asp Arg Phe Gly Gln Gln Pro Lys Phe His Arg Phe Val Tyr Leu Pro
625                 630                 635                 640

Glu Ser Ser Asp Ser Ala Thr Leu Arg Glu Leu Arg Gly Asp Thr Pro
                645                 650                 655

Tyr Leu Val Cys Val Glu Gly Val Leu Gly Arg Val Cys Pro Val
                660                 665                 670

Ala Pro Arg Asp His Cys Ala Gly Leu Val Thr Leu Pro Glu Ala Gly
                675                 680                 685

Ser Arg Gly Gly Val Asp Tyr Gln Leu
            690                 695

<210> SEQ ID NO 3
<211> LENGTH: 809
<212> TYPE: PRT
<213> ORGANISM: Mus musculus

<400> SEQUENCE: 3

Met Glu Gly Val Gly Ala Val Arg Phe Trp Leu Val Val Cys Gly Cys
1               5                   10                  15

Leu Ala Phe Pro Pro Arg Ala Glu Ser Val Cys Pro Glu Arg Cys Asp
                20                  25                  30

Cys Gln His Pro Gln His Leu Leu Cys Thr Asn Arg Gly Leu Arg Ala
            35                  40                  45

Val Pro Lys Thr Ser Ser Leu Pro Ser Pro Gln Asp Val Leu Thr Tyr
        50                  55                  60

Ser Leu Gly Gly Asn Phe Ile Thr Asn Ile Thr Ala Phe Asp Phe His
65              70                  75                  80

Arg Leu Gly Gln Leu Arg Arg Leu Asp Leu Gln Tyr Asn Gln Ile Arg
                85                  90                  95

Ser Leu His Pro Lys Thr Phe Glu Lys Leu Ser Arg Leu Glu Glu Leu
            100                 105                 110

Tyr Leu Gly Asn Asn Leu Leu Gln Ala Leu Val Pro Gly Thr Leu Ala
        115                 120                 125

Pro Leu Arg Lys Leu Arg Ile Leu Tyr Ala Asn Gly Asn Glu Ile Gly
    130                 135                 140

Arg Leu Ser Arg Gly Ser Phe Glu Gly Leu Glu Ser Leu Val Lys Leu
145                 150                 155                 160

Arg Leu Asp Gly Asn Val Leu Gly Ala Leu Pro Asp Ala Val Phe Ala
                165                 170                 175

Pro Leu Gly Asn Leu Leu Tyr Leu His Leu Glu Ser Asn Arg Ile Arg
            180                 185                 190

Phe Leu Gly Lys Asn Ala Phe Ser Gln Leu Gly Lys Leu Arg Phe Leu
        195                 200                 205

Asn Leu Ser Ala Asn Glu Leu Gln Pro Ser Leu Arg His Ala Ala Thr
    210                 215                 220

Phe Val Pro Leu Arg Ser Leu Ser Thr Leu Ile Leu Ser Ala Asn Ser
225                 230                 235                 240

Leu Gln His Leu Gly Pro Arg Val Phe Gln His Leu Pro Arg Leu Gly
                245                 250                 255

Leu Leu Ser Leu Ser Gly Asn Gln Leu Thr His Leu Ala Pro Glu Ala
            260                 265                 270

Phe Trp Gly Leu Glu Ala Leu Arg Glu Leu Arg Leu Glu Gly Asn Arg
        275                 280                 285

Leu Asn Gln Leu Pro Leu Thr Leu Leu Glu Pro Leu His Ser Leu Glu
```

```
                    290                 295                 300
Ala Leu Asp Leu Ser Gly Asn Glu Leu Ser Ala Leu His Pro Ala Thr
305                 310                 315                 320

Phe Gly His Gln Gly Arg Leu Arg Glu Leu Ser Leu Arg Asp Asn Ala
                    325                 330                 335

Leu Ser Ala Leu Ser Gly Asp Ile Phe Ala Ala Ser Pro Ala Leu Tyr
                340                 345                 350

Arg Leu Asp Leu Asp Gly Asn Gly Trp Thr Cys Asp Cys Arg Leu Arg
                355                 360                 365

Gly Leu Lys Arg Trp Met Gly Asn Trp His Ser Gln Gly Arg Leu Leu
            370                 375                 380

Thr Val Phe Val Gln Cys Arg His Pro Pro Ala Leu Arg Gly Lys Tyr
385                 390                 395                 400

Leu Asp Tyr Leu Asp Asp Gln Leu Leu Gln Asn Gly Ser Cys Val Asp
                    405                 410                 415

Pro Ser Pro Ser Pro Thr Ala Gly Ser Arg Gln Trp Pro Leu Pro Thr
                420                 425                 430

Ser Ser Glu Glu Gly Met Thr Pro Pro Ala Gly Leu Ser Gln Glu Leu
            435                 440                 445

Pro Leu Gln Pro Gln Pro Gln Pro Gln Arg Gly Arg Leu Leu Pro
450                 455                 460

Gly Val Ala Trp Gly Ala Ala Lys Glu Leu Val Gly Asn Arg Ser
465                 470                 475                 480

Ala Leu Arg Leu Ser Arg Arg Gly Pro Gly Pro His Gln Gly Pro Ser
                485                 490                 495

Ala Ala Ala Pro Gly Ser Ala Pro Gln Ser Leu Asp Leu His Glu Lys
                500                 505                 510

Pro Gly Arg Gly Arg His Thr Arg Ala Asn Leu Ser Gln Thr Glu Pro
            515                 520                 525

Thr Pro Thr Ser Glu Pro Ala Ser Gly Thr Pro Ser Ala Arg Asp Ser
            530                 535                 540

Trp Gln Arg Ala Ala Lys Gln Arg Leu Ala Ser Glu Gln Gln Glu Ser
545                 550                 555                 560

Ala Val Gln Ser Val Ser Gly Val Gly Leu Pro Pro Leu Val Ser Asp
                565                 570                 575

Pro Cys Asp Phe Asn Lys Phe Ile Leu Cys Asn Leu Thr Val Glu Ala
                580                 585                 590

Val Ser Ala Asn Ser Ala Ser Val Arg Trp Ala Val Arg Glu His Arg
            595                 600                 605

Ser Pro Arg Pro Gln Gly Gly Ala Arg Phe Arg Leu Leu Phe Asp Arg
            610                 615                 620

Phe Gly Gln Gln Pro Lys Phe Gln Arg Phe Val Tyr Leu Pro Glu Arg
625                 630                 635                 640

Ser Asp Ser Ala Thr Leu His Glu Leu Arg Gly Asp Thr Pro Tyr Leu
                645                 650                 655

Val Cys Val Glu Gly Val Leu Gly Gly Arg Val Cys Pro Val Ala Pro
                660                 665                 670

Arg Asp His Cys Ala Gly Leu Val Thr Leu Pro Glu Ala Gly Gly Arg
            675                 680                 685

Gly Gly Val Asp Tyr Gln Leu Leu Thr Leu Val Leu Ala Val Asn
            690                 695                 700

Ala Leu Leu Val Leu Ala Leu Ala Ala Trp Gly Ser Arg Trp Leu
705                 710                 715                 720
```

```
Arg Arg Lys Leu Arg Ala Arg Arg Lys Gly Ala Pro Val His Val
            725                 730                 735

Arg His Met Tyr Ser Thr Arg Arg Pro Leu Arg Ser Met Gly Thr Gly
                740                 745                 750

Val Ser Ala Asp Phe Ser Gly Phe Gln Ser His Arg Pro Arg Thr Thr
            755                 760                 765

Val Cys Ala Leu Ser Glu Ala Asp Leu Ile Glu Phe Pro Cys Asp Arg
            770                 775                 780

Phe Met Asp Ser Thr Gly Gly Thr Ser Gly Ser Leu Arg Arg Glu
785                 790                 795                 800

Asp His Leu Leu Gln Arg Phe Ala Asp
                805

<210> SEQ ID NO 4
<211> LENGTH: 799
<212> TYPE: PRT
<213> ORGANISM: Homo sapiens

<400> SEQUENCE: 4

Met Glu Leu Asn Phe Tyr Lys Ile Pro Asp Asn Leu Pro Phe Ser Thr
1               5                   10                  15

Lys Asn Leu Asp Leu Ser Phe Asn Pro Leu Arg His Leu Gly Ser Tyr
                20                  25                  30

Ser Phe Phe Ser Phe Pro Glu Leu Gln Val Leu Asp Leu Ser Arg Cys
            35                  40                  45

Glu Ile Gln Thr Ile Glu Asp Gly Ala Tyr Gln Ser Leu Ser His Leu
        50                  55                  60

Ser Thr Leu Ile Leu Thr Gly Asn Pro Ile Gln Ser Leu Ala Leu Gly
65                  70                  75                  80

Ala Phe Ser Gly Leu Ser Ser Leu Gln Lys Leu Val Ala Val Glu Thr
                85                  90                  95

Asn Leu Ala Ser Leu Glu Asn Phe Pro Ile Gly His Leu Lys Thr Leu
            100                 105                 110

Lys Glu Leu Asn Val Ala His Asn Leu Ile Gln Ser Phe Lys Leu Pro
        115                 120                 125

Glu Tyr Phe Ser Asn Leu Thr Asn Leu Glu His Leu Asp Leu Ser Ser
    130                 135                 140

Asn Lys Ile Gln Ser Ile Tyr Cys Thr Asp Leu Arg Val Leu His Gln
145                 150                 155                 160

Met Pro Leu Leu Asn Leu Ser Leu Asp Leu Ser Leu Asn Pro Met Asn
                165                 170                 175

Phe Ile Gln Pro Gly Ala Phe Lys Glu Ile Arg Leu His Lys Leu Thr
            180                 185                 190

Leu Arg Asn Asn Phe Asp Ser Leu Asn Val Met Lys Thr Cys Ile Gln
        195                 200                 205

Gly Leu Ala Gly Leu Glu Val His Arg Leu Val Leu Gly Glu Phe Arg
    210                 215                 220

Asn Glu Gly Asn Leu Glu Lys Phe Asp Lys Ser Ala Leu Glu Gly Leu
225                 230                 235                 240

Cys Asn Leu Thr Ile Glu Glu Phe Arg Leu Ala Tyr Leu Asp Tyr Tyr
                245                 250                 255

Leu Asp Asp Ile Ile Asp Leu Phe Asn Cys Leu Thr Asn Val Ser Ser
            260                 265                 270

Phe Ser Leu Val Ser Val Thr Ile Glu Arg Val Lys Asp Phe Ser Tyr
        275                 280                 285
```

```
Asn Phe Gly Trp Gln His Leu Glu Leu Val Asn Cys Lys Phe Gly Gln
    290                 295                 300

Phe Pro Thr Leu Lys Leu Lys Ser Leu Lys Arg Leu Thr Phe Thr Ser
305                 310                 315                 320

Asn Lys Gly Gly Asn Ala Phe Ser Glu Val Asp Leu Pro Ser Leu Glu
                325                 330                 335

Phe Leu Asp Leu Ser Arg Asn Gly Leu Ser Phe Lys Gly Cys Cys Ser
                340                 345                 350

Gln Ser Asp Phe Gly Thr Thr Ser Leu Lys Tyr Leu Asp Leu Ser Phe
            355                 360                 365

Asn Gly Val Ile Thr Met Ser Ser Asn Phe Leu Gly Leu Glu Gln Leu
    370                 375                 380

Glu His Leu Asp Phe Gln His Ser Asn Leu Lys Gln Met Ser Glu Phe
385                 390                 395                 400

Ser Val Phe Leu Ser Leu Arg Asn Leu Ile Tyr Leu Asp Ile Ser His
                405                 410                 415

Thr His Thr Arg Val Ala Phe Asn Gly Ile Phe Asn Gly Leu Ser Ser
                420                 425                 430

Leu Glu Val Leu Lys Met Ala Gly Asn Ser Phe Gln Glu Asn Phe Leu
    435                 440                 445

Pro Asp Ile Phe Thr Glu Leu Arg Asn Leu Thr Phe Leu Asp Leu Ser
450                 455                 460

Gln Cys Gln Leu Glu Gln Leu Ser Pro Thr Ala Phe Asn Ser Leu Ser
465                 470                 475                 480

Ser Leu Gln Val Leu Asn Met Ser His Asn Asn Phe Phe Ser Leu Asp
                485                 490                 495

Thr Phe Pro Tyr Lys Cys Leu Asn Ser Leu Gln Val Leu Asp Tyr Ser
                500                 505                 510

Leu Asn His Ile Met Thr Ser Lys Lys Gln Glu Leu Gln His Phe Pro
    515                 520                 525

Ser Ser Leu Ala Phe Leu Asn Leu Thr Gln Asn Asp Phe Ala Cys Thr
530                 535                 540

Cys Glu His Gln Ser Phe Leu Gln Trp Ile Lys Asp Gln Arg Gln Leu
545                 550                 555                 560

Leu Val Glu Val Glu Arg Met Glu Cys Ala Thr Pro Ser Asp Lys Gln
                565                 570                 575

Gly Met Pro Val Leu Ser Leu Asn Ile Thr Cys Gln Met Asn Lys Thr
                580                 585                 590

Ile Ile Gly Val Ser Val Leu Ser Val Leu Val Val Ser Val Val Ala
    595                 600                 605

Val Leu Val Tyr Lys Phe Tyr Phe His Leu Met Leu Leu Ala Gly Cys
610                 615                 620

Ile Lys Tyr Gly Arg Gly Glu Asn Ile Tyr Asp Ala Phe Val Ile Tyr
625                 630                 635                 640

Ser Ser Gln Asp Glu Asp Trp Val Arg Asn Glu Leu Val Lys Asn Leu
                645                 650                 655

Glu Glu Gly Val Pro Pro Phe Gln Leu Cys Leu His Tyr Arg Asp Phe
                660                 665                 670

Ile Pro Gly Val Ala Ile Ala Ala Asn Ile Ile His Glu Gly Phe His
                675                 680                 685

Lys Ser Arg Lys Val Ile Val Val Ser Gln His Phe Ile Gln Ser
    690                 695                 700

Arg Trp Cys Ile Phe Glu Tyr Glu Ile Ala Gln Thr Trp Gln Phe Leu
705                 710                 715                 720
```

```
Ser Ser Arg Ala Gly Ile Ile Phe Ile Val Leu Gln Lys Val Glu Lys
            725                 730             735

Thr Leu Leu Arg Gln Gln Val Glu Leu Tyr Arg Leu Leu Ser Arg Asn
            740             745             750

Thr Tyr Leu Glu Trp Glu Asp Ser Val Leu Gly Arg His Ile Phe Trp
        755             760             765

Arg Arg Leu Arg Lys Ala Leu Leu Asp Gly Lys Ser Trp Asn Pro Glu
    770             775             780

Gly Thr Val Gly Thr Gly Cys Asn Trp Gln Glu Ala Thr Ser Ile
785             790             795
```

METHODS FOR SUPPRESSING TOLL-LIKE RECEPTOR 4 (TLR4) FUNCTION USING TLR14 ANTAGONISTS

This application is the U.S. national phase application of International Application No. PCT/EP2007/061182, filed Oct. 18, 2007, which designated the U.S. and claims the benefit of Great Britain Patent Application No. GB0620705.4, filed Oct. 18, 2006, the disclosures of which are incorporated herein by reference.

FIELD OF THE INVENTION

The present invention relates to compounds which modulate Toll-like Receptor 4 function. The invention further relates to assay methods which serve to identify compounds which modulate Toll-like Receptor function, and in particular the signalling mediated by a co-receptor complex comprising Toll-like Receptor 4 and Toll-like Receptor 14.

BACKGROUND TO THE INVENTION

The Toll-like Receptor (TLR) superfamily plays a central role in the recognition of invading pathogens and the initiation of an immune response. Each TLR recognises a distinct pathogen-associated molecular pattern (PAMP) leading to the activation of a signalling cascade, which in turn activates the transcription factor NF-κB and also the mitogen-activated protein kinases (MAPKs), p38, c-jun, N terminal kinase (JNK) and p42/44. Toll-like Receptor 4 (TLR-4, TLR4) also activates a further pathway which culminates in the activation of the transcription factor IFN-regulated factor-3 (IRF3), which binds to the interferon-sensitive response element (ISRE), inducing a subset of genes including interferon beta. The TLRs are members of a larger superfamily, called the interleukin-1 receptor (IL-1R)/TLR superfamily, that also contains the IL-1R1 subgroup and the TIR domain-containing adaptor subgroup. All three subgroups possess a cytoplasmic Toll/IL-1 receptor (TIR) domain, which is essential for signalling. The TLRs possess extracellular leucine rich repeats, while the IL-1R1 subgroup have extracellular immunoglobin domains.

The inventors have surprisingly identified that Toll-like Receptor 14, a protein characterised as comprising the amino acid sequence of SEQ ID NO:1 in the human form, or the amino acid sequence of SEQ ID NO:3 in the murine form, acts as a co-receptor with the Toll-like Receptor, Toll-like Receptor 4 (TLR4). The inventors have shown that signalling mediated by TLR4 following the activation of TLR4 with endotoxin (a defined pathogen-associated molecular pattern (PAMP) of TLR4) is suppressed in cells where there is an inhibition of TLR14 expression, for example as a result of siRNA mediated TLR14 knockdown.

TLR4 has a recognised importance in relation to endotoxin-mediated signalling. Endotoxin-mediated signalling through TLR4 can result in conditions such as septicaemia and sepsis. It is therefore desirable to identify compounds and agents which can modulate the function of TLR4, and in particular which suppress TLR4 activation and signalling in response to endotoxins, such as lipopolysaccharide (LPS).

SUMMARY OF THE INVENTION

According to the present invention there is provided a method for suppressing Toll-like Receptor 4 activation and signalling, the method comprising the step of:

providing a therapeutically effective amount of a compound which inhibits the expression or biological function of a protein comprising the amino acid sequence of SEQ ID NO:1, and administering the same to a subject in need of such treatment.

In certain embodiments, the protein which comprises the amino acid sequence of SEQ ID NO:1 is Toll-like Receptor 14.

The amino acid sequence of the human form of Toll-like Receptor 14 has previously been defined. This is provided herein as SEQ ID NO:1.

As herein defined "Toll-like Receptor 4 (TLR4) activation" means that TLR4 is bound by, or associates with at least one further molecule which results in signalling being mediated by the TIR domain of TLR4. Furthermore, as defined herein, the term "Toll-like Receptor 4 signalling" means the activation of at least one downstream signalling pathway which has resulted from the activation of Toll-Like Receptor 4. Typically, the signalling is an intracellular signalling cascade which is initiated by the TIR domain of TLR4. The signalling cascade induced by TLR4 may result in activation of the transcription factors such as NF-KB, or interferon regulated factor 3. TLR4 mediated signalling may further activate mitogen-activated protein kinases (MAPKs), p38, c-jun, N terminal kinase (JNK) and p42/44.

Toll-like Receptor 4 is known to be activated in response to endotoxins, such as lipopolysaccharide (LPS) derived from gram negative bacteria. Toll-like Receptor 4 does not however directly associate with LPS. Rather, TLR4 uses the molecule MD-2 as an adapter molecule to facilitate the binding of LPS. The inventors theorise that Toll-like Receptor 14 binds LPS. The bound LPS is then transferred from TLR14 to a pre-formed complex of TLR4 and MD-2. This defined mechanism of action for TLR14 is similar to that ascribed to CD14.

Accordingly, the method of the present invention, in suppressing TLR4 mediated signalling and activation of the immune system is mediated by preventing the association of Toll-like Receptor 14 with Toll-like Receptor 4, such that Toll-like Receptor 4 activation and signalling cannot result.

In certain embodiments, the compound which inhibits the expression or biological function of a protein comprising the amino acid sequence of SEQ ID NO:1 (Toll-like Receptor 14) is selected from at least one of the groups comprising, but not limited to: proteins, peptides, peptidomimetics, nucleic acids, polynucleotides, polysaccharides, oligopeptides, carbohydrates, lipids, small molecule compounds, and naturally occurring compounds.

In certain embodiments, the compound which inhibits the expression or biological function of Toll-like Receptor 14 is an inhibitory nucleic acid. Such a nucleic acid functions to prevent the expression of the Toll-like Receptor 14 protein. Examples of suitable inhibitory nucleic acids include, but are not limited to: anti-sense oligonucleotides, anti-sense DNA, anti-sense RNA, ribozyme, iRNA, miRNA, sRNA, and shRNA.

As herein defined, the term "inhibition of biological function" means preventing at least one activity of TLR14 which results in TLR4 activation and signalling, for example the ability of TLR14 to bind to LPS, or the ability of TLR14 to complex with TLR4 as a co-receptor.

In certain further embodiments, Toll-like Receptor 4 activation and signalling is inhibited by means of an antibody, or a similar binding compound, which inhibits TLR14 complexing with TLR4 as a co-receptor, and thus suppresses TLR4 activation.

In certain embodiments, the antibody may bind to TLR14, to TLR4 or to both. Binding of the antibody to an epitope present on TLR4 and/or TLR14 results in an inhibition of TLR4 activation and signalling.

In certain embodiments, the compound which inhibits the biological function of Toll-like Receptor 14 is a soluble form of Toll-like Receptor 14. Said soluble form of Toll-like Receptor 14 is not membrane bound and may, for example, be lacking in all or a substantial number of the amino acid residues which comprise the extracellular domain of the Toll-like Receptor 14 protein as defined in SEQ ID NO:1.

In certain embodiments, the method of this aspect of the invention further comprises the step of administering to the subject a therapeutically effective amount of a composition which inhibits the expression or biological function of CD14.

According to a second aspect of the present invention, there is provided a pharmaceutical composition for use in suppressing Toll-like Receptor 4 activation and signalling, the pharmaceutical composition comprising a compound which inhibits the expression or biological function of Toll-like Receptor 14 along with at least one pharmaceutically acceptable diluent, excipient or carrier.

In certain embodiments, the compound which inhibits the expression or biological function of Toll-like Receptor 14 is selected from at least one of the group comprising, but not limited to: proteins, peptides, peptidomimetics, nucleic acids, polynucleotides, polysaccharides, oligopeptides, carbohydrates, lipids, small molecule compounds, and naturally occurring compounds.

In certain embodiments, the pharmaceutical composition may comprise a combined medicament, the primary component of which is a compound which inhibits the expression or biological function of Toll-like Receptor 14, said combined medicament comprising as a secondary component, a compound which inhibits the expression or biological function of CD14. Such a combined medicament will achieve global suppression of LPS mediated TLR4 activation.

According to a still further aspect of the present invention, there is provided the use of a compound which inhibits the expression or biological function of Toll-like Receptor 14 in the preparation of a medicament for the treatment of a condition which is mediated by Toll-like Receptor 4 activation and signalling.

In certain embodiments, the condition which is mediated by Toll-like Receptor 4 activation and signalling is septicaemia or septic shock.

According to a yet further aspect of the present invention there is provided a composition comprising a compound which inhibits the expression or biological function of Toll-like Receptor 14 for use in a medicament for the treatment of a condition which is caused by Toll-like Receptor 4 activation and signalling.

In certain embodiments, the condition which is mediated by Toll-like Receptor 4 activation and signalling is septicaemia or septic shock.

In various further aspects, the present invention extends to assay methods for use in identifying compounds which inhibit the expression or biological function of TLR14. In turn, further aspects of the invention extend to compositions comprising the compounds identified by said assay methods, and further to the use of said compounds and compositions in the suppression of TLR4 activation and signalling.

Accordingly, a yet further aspect of the present invention provides an assay method for the identification of a compound which inhibits the association of Toll-like Receptor 14 with Toll-like Receptor 4 as a co-receptor, said method comprising the steps of:

providing first and second cellular samples comprising Toll-like Receptor 4 and Toll-like Receptor 14, contacting said first and second samples with endotoxin which binds to Toll-like Receptor 14 under conditions permissive of allowing the Toll-like Receptor 14 when bound to the endotoxin to associate with Toll-like Receptor 4, contacting said first sample with a candidate modulator compound under conditions permissive of binding of said compound, and monitoring the activation status of the Toll-like Receptor 4 receptor complex through a comparison of the level of downstream activation between said first and second samples, wherein a reduction in Toll-like Receptor 4 signalling between said first sample and said second sample identifies the modulator as an inhibitor of the association of Toll-like Receptor 4 and Toll-like Receptor 14.

In certain embodiments, the modulator may be selected from at least one of the groups comprising, but not limited to: proteins, peptides, peptidomimetics, nucleic acids, polynucleotides, polysaccharides, oligopeptides, carbohydrates, lipids, small molecule compounds, and naturally occurring compounds.

In certain embodiments, the candidate compound suppresses TLR14 receptor complex binding and association with TLR4. In certain embodiments, the modulator compound suppresses TLR14 expression.

In certain embodiments, the molecule which binds to TLR14, and activates the TLR4 receptor is lipopolysaccharide (LPS).

In one embodiment, the downstream activation of the TLR4 receptor is monitored in terms of monitoring markers indicative of Toll-like Receptor activity. Examples of such markers include; NF-kappaB activation, and IRF3 protein activation.

In various further aspects, the present invention extends to compositions which comprise the TLR14 inhibitory compounds which are identified by the assay method of the foregoing aspect of the invention.

In various further aspects, the invention extends to the use of the compounds identified by the foregoing assay method in methods for the suppression of TLR4 activation and signalling.

In various further aspects, the invention extends to assay methods for the identification of compounds which inhibit the ability of TLR14 to complex as a co-receptor with TLR4.

In a further aspect, the invention extends to an assay method which identifies modulators of TLR4 in terms of monitoring the association of the Toll-like Receptor 4 with Toll-like Receptor 14 as a co-receptor. Such an assay would, for example, be based upon FRET (fluorescence resonance energy transfer), a method used in the quantification of molecular dynamics in protein to protein interactions.

In order to monitor association and complex formation between two molecules, one of the molecules is labelled with a fluorophore donor molecule, while the other is labelled with a fluorophore acceptor molecule. When the two molecules interact, the donor emission is transferred to the acceptor molecule. This results in the acceptor molecule emitting a light output that can be monitored. When the donor and acceptor are in close proximity, say 1-10 nm, the two molecules interact, with the resulting light output being monitored. The emission from the acceptor molecule is due to the intermolecular fluorescence resonance energy transfer from the donor to the acceptor molecule. Examples of fluorophore molecules used in such assays are cyan fluorescent protein (CFP) and yellow fluorescent protein (YFP).

Accordingly in a further aspect of the present invention there is provided a method for the identification of a compound which acts as a modulator of Toll-like Receptor 4 activation and signalling, said method comprising the steps of:
 providing first and second cellular samples containing Toll-like Receptor 4 and Toll-like Receptor 14,
 labelling the Toll-like Receptor 4 with a first fluorophore molecule and the Toll-like Receptor 14 with a second fluorophore molecule,
 contacting said first sample with a molecule which causes activation of the Toll-like Receptor 4 receptor,
 contacting said first and second samples with a candidate modulator agent under conditions permissive of binding of Toll-like Receptor 4 and/or Toll-like Receptor 14, and
 monitoring the binding status and/or activation of the Toll-like Receptor 4 receptor by monitoring the fluorescence of the fluorophores,
wherein a change in the fluorescence identifies the candidate modulator agent as a modulator of the Toll-like Receptor 4 activation and signalling.

In certain embodiments, the molecule which causes activation of Toll-like Receptor 4 is an endotoxin, such as LPS, which binds to Toll-like Receptor 14, this allowing Toll-like Receptor 14 to associate with Toll-like Receptor 4 in a complex as a co-receptor.

In certain embodiments, the assay methods of the invention are in-vitro assay methods.

In certain embodiments, the modulator compound which is identified by the assay method of this aspect of the invention is a compound which suppresses the activation and/or down-stream signalling of Toll-like Receptor 4. In certain embodiments, the modulator compound which is identified by the assay method of this aspect of the invention is a compound which enhances the activation and/or down-stream signalling of Toll-like Receptor 4.

A reduction in light emission from the fluorophore is indicative of a candidate modulator inhibiting or suppressing the TLR4 receptor activity.

In certain embodiments, the modulator compound is an antibody, peptidomimetic, polypeptide, or small molecule which binds to either Toll-like Receptor 14 or Toll-like Receptor 4, this binding preventing a complex forming between TLR4 and TLR14.

In certain embodiments, the assay can be performed using the bead-based ALPHASCREEN technique (Perkin Elmer) as described in Ullman et al. PNAS, vol 91, pp 5426-5430, June 1994. The AlphaScreen assay contains two bead types, donor and acceptor beads. Beads can be coupled to the molecules of interest, interaction between the molecules captured on the beads leads to an energy transfer from one bead to the other resulting in a fluorescent/luminescent signal. Advantageously the AlphaScreen assay system permits for high throughout screening and accordingly the assay methods of the present invention which utilise FRET can be used in this format.

Advantageously the AlphaScreen assay system permits for high throughput screening and accordingly the assay methods of the present invention which utilise FRET can be used in HTS screening methods to facilitate the identification of modulator agent compounds.

The principles of the FRET based assay can be extended to the identification of candidate modulator agents which disrupt the co-receptor complex formed between TLR4 and TLR14.

In various further aspects, the invention extends to compositions comprising modulatory compounds identified using the assay method of the foregoing aspect of the invention. The invention further extends to the use of said compositions and of said modulator compounds for use in methods and compositions for preventing the association of Toll-like Receptor 14 with Toll-like Receptor 4 as a co-receptor.

In certain further aspects, various assays for measuring TLR4 activation and/or identifying modulators of TLR4 activation can be used. For example, a screening assay for TLR4 stimulation has been described wherein cells in culture are transfected with two plasmids, one carrying the gene for human TLR4 and the other, a detector plasmid, carrying a promoter that binds to NFkappa B upstream of a luciferase gene (Vogel, S. J. Biol. Chem. 2003 278:222506). Alternatively a yeast two-hybrid system can be used for screening for TLR4 activation.

Accordingly to a yet further aspect of the present invention there is provided a method for the identification of modulator agents which disrupt the association of Toll-like Receptor 14 with Toll-like Receptor 4, the method comprising the steps of:
 providing first and second cellular samples containing TLR4 and TLR14,
 labelling the TLR4 with a first fluorophore molecule and the TLR14 with a second fluorophore molecule,
 contacting said first sample with a molecule which binds TLR14 and activates TLR4 and accordingly causes association of TLR4 with TLR14,
 contacting said first sample with a candidate modulator compound under conditions permissive to allow binding of the modulator compound to TLR14 and/or TLR4, and
 monitoring the binding status and/or activation of the TLR4 receptor by monitoring the fluorescence of the fluorophores,
wherein a change in the fluorescence identifies the candidate modulator agent acts to disrupt the co-receptor complex formed between TLR4 and TLR14, thus identifying the modulator agent as a modulator of the TLR4 receptor.

In certain embodiments, the molecule which causes activation of TLR4 is an endotoxin, for example LPS. Typically, said endotoxin binds to TLR14, this allowing TLR14 to associate with TLR4 in a co-receptor complex.

A reduction in light emission from the fluorophore is indicative of a candidate modulator inhibiting or suppressing the TLR4 receptor activity.

In various further aspects, the invention extends to compositions containing the modulatory compounds identified by the assay methods of the foregoing aspect of the invention. The invention further extends to the use of said compositions and modulator compounds in methods for use in preventing endotoxin-mediated TLR4 signalling.

In further aspects the invention extends to assay methods wherein the binding between lipopolysaccharide (LPS, endotoxin) and TLR14 is monitored using the FRET system. Each of LPS and TLR14 would be labelled with a separate, but complimentary fluorophore donor or acceptor molecule respectively. Binding of LPS with the TLR14 receptor would result in emission of light from the acceptor molecule due to the intermolecular fluorescence resonance energy transfer from the donor to the acceptor molecule. The assay can be used to identify modulatory agents which disrupt the LPS/TLR14 complex, as the FRET signal emission will change. The surprising observation by the present inventors that downstream signalling from the TLR4 receptor complex is substantially suppressed when TLR14 is functionally blocked, or its expression is suppressed, indicates that the suppression of TLR14 expression or function by a modulator agent will result in a reduction in downstream signalling following the binding of TLR4 by a ligand.

A secondary reporter gene assay can further be performed with selected LPS antagonists to look at the signal which results from TLR4 signalling following the binding of LPS thereto.

Conditions known as sepsis, septic shock and septicaemia are potentially lethal conditions which result from LPS-induced activation of Toll-like Receptor 4. The inventors have therefore identified the utility of the present invention in compounds and methods for the treatment and prophylaxis of conditions such as sepsis, septic shock and septicaemia.

Accordingly, a further aspect of the present invention provides a method for the treatment and/or prophylaxis of septicaemia or septic shock, the method comprising the steps of:
  providing a therapeutically effective amount of a compound which inhibits the expression or biological function of Toll-like Receptor 14, and
  administering the same to a subject in need of such treatment.

In certain embodiments, the method comprises the further step of administering to the subject a therapeutically effective amount of a composition which inhibits the expression or biological function of CD14.

According to a still further aspect of the present invention, there is provided the use of a compound which inhibits the expression or biological function of Toll-like Receptor 14 in the preparation of a medicament for the treatment of septicaemia or septic shock.

According to a yet further aspect of the present invention there is provided a composition comprising a compound which inhibits the expression or biological function of Toll-like Receptor 14 for use in a medicament for the treatment of septicaemia or septic shock.

The conditions of septicaemia or septic shock are caused by endotoxin, such as LPS, which is derived from gram negative bacteria. In certain embodiments, the gram negative bacteria is selected from the list comprising, but not limited to: *Neisseria meningitides, Escherivchia coli, Pseudomonas aeruginosa, Haemophilia influenzae, Salmonella typhimurium*, and *Francisella tularensis*.

In certain embodiments, the compound which inhibits the expression or biological function of Toll-like Receptor 14 is selected from at least one of the group comprising, but not limited to: proteins, peptides, peptidomimetics, nucleic acids, polynucleotides, polysaccharides, oligopeptides, carbohydrates, lipids, small molecule compounds, and naturally occurring compounds.

In various further aspects, the invention extends to assay methods for use in identifying compounds which inhibit TLR14 expression or biological activity, and which therefore have utility in the treatment and/or prophylaxis of sepsis.

In certain further aspects, the present invention extends to compositions comprising the inhibitory compounds determined by the assay of the foregoing aspect of the invention for use in the treatment of septicaemia and septic shock.

Given the important role of activated TLR4 in endotoxin related septicemia and septic shock, it is expected that test agents identified as inhibitors of TLR4 activation in the above described methods of the present invention will be useful in preventing or treating endotoxin-related septicemia and/or septic shock.

Thus the present invention also provides compositions for treating septicaemia and/or septic shock in a subject by administering to the subject an agent which inhibits activation of Toll-like receptor 4 activity as determined by the assay methods of the invention. Such methods and compositions may be used in subjects exhibiting symptoms of septicemia and/or septic shock. Such compositions and methods can also be used prophylactically in subjects at high risk of developing septicemia or septic shock including, but not limited to patients undergoing major surgery, and in particular operations in the gut area, as well as immunosuppressed subjects undergoing surgical procedures.

The invention further extends to the use of the compounds identified by such assays for the treatment of sepsis.

Endotoxins are composed of a lipopolysaccharide (LPS) complex which includes Lipid A and polysaccharide. The lipopolysaccharide (endotoxin, LPS) of Gram-negative bacteria triggers cellular and physiological responses such as those observed during Gram-negative sepsis. Cells of the immune/inflammatory systems respond to LPS by a pathway involving both plasma and membrane proteins.

Accordingly, a method of down-regulating or inhibiting the TLR4 mediated immune response pathway would be desirable as a treatment method for LPS mediated conditions such as sepsis. The present invention may be used in the treatment of LPS-mediated conditions.

The assays of the present invention and modulator agents which are identified thereby have specific utility in the treatment in a number of medical conditions, most specifically endotoxin and LPS mediated conditions, for example sepsis.

Accordingly, to a yet further aspect of the present invention, there is provided an assay for identifying compounds suitable for use in the treatment of endotoxin mediated conditions, said assay comprising the steps of:
  providing a candidate compound,
  bringing the candidate compound into contact with the TLR4 receptor complex, said complex comprising TLR14 bound to endotoxin,
  monitoring the light emission from fluorophore moieties which are conjoined to the TLR4 and TLR14 components of the receptor complex, wherein modulation of light emission level from the fluorophore is indicative of the utility of that compound in suppressing signalling through the TLR4 receptor complex.

In one embodiment the endotoxin mediated condition is sepsis or septic shock.

A yet further aspect of the present invention comprises a composition for the treatment or prophylaxis of sepsis comprising a TLR14 inhibitory compound identified by the foregoing assay method of the present invention.

The inventors have further observed that Toll-like Receptor 14 is expressed in the brain. Expression of TLR14 is seen in the cortex and hippocampus of mice in an experimental autoimmune encephalomyelitis (EAE) model. Expression of TLR14 is also observed in the cerebellum of the same model. On the basis of the mechanism of action of TLR14 as defined herein by the inventors, the inventors further predict that Toll-like Receptor 14 has a role in TLR4-mediated inflammatory signalling in the brain. TLR14 may therefore have involvement in endotoxin mediated Toll-like Receptor 4 signalling in the brain. Accordingly, in various further aspects, the invention extends to inhibiting such TLR4 mediated signalling by inhibiting the expression of, or blocking the biological functional activity of TLR14 in the brain. Accordingly, in various further aspects the invention extends to compounds, compositions and further to the use of said compounds and compositions in methods for suppressing endotoxin mediated TLR4 inflammatory signalling in the brain.

A yet further aspect of the present invention provides a method of treating an aberrant immune response mediated by Toll-like Receptor 4 activation and signalling, the method comprising the steps of:

providing a compound which inhibits the association of Toll-like Receptor 14 with Toll-like Receptor 4, and administering a therapeutically useful amount of the same to a subject in need of treatment.

The aberrant immune response may be any immune mediated response which is undesirable. In certain embodiments, the aberrant immune response results in a condition, such as septicaemia, or septic shock. In certain embodiments, the sepsis is gram negative sepsis, derived from binding of endotoxin, such as lipopolysaccharide derived from gram negative bacteria, to Toll-like Receptor 4.

Assays

The invention extends to assay systems and screening methods for determining modulators of TLR14 protein activation and further to methods for monitoring TLR14 activation. As used herein, an "assay system" encompasses all the components required for performing and analysing results of an assay that detects and/or measures a particular event or events.

It is preferred, though not essential, that the screening assays employed in the present invention are high throughput or ultra high throughput and thus provide an automated, cost-effective means of screening.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

BRIEF DESCRIPTION OF DRAWINGS

The present invention will now be described with reference to the following examples which are provided for the purpose of illustration and are not intended to be construed as being limiting on the present invention, and further, with reference to the figures.

FIG. 1 shows that TLR14 enhances LPS signalling. Human astrocytoma cells (U373s) were transfected with 50 ng of empty control vector or TLR14 expression plasmid together with an NF-kB reporter construct. After 24 hours, the cells were stimulated with LPS (100 ng/ml) for 6 hours before being harvested and analysed for reporter gene activity, U373s were stimulated with LPS (100 ng/ml) in the presence or absence of over-expressed TLR14 before being harvested and analysed for reporter gene activity. TLR14 enhanced LPS induced NF-κB reporter gene expression when compared to non-transfected cells, FIG. 2 shows that knockdown of TLR14 abolishes LPS induced IκB degradation in U373 astrocytoma cells. U373s were transfected with siRNA specific to TLR14 (Dharmacon). After 48 hours, knockdown of TLR14 was confirmed by western blotting (FIG. 2A). A non-targeting siRNA was used as a negative control to ensure that the siRNA to TLR14 was specific. Cells were treated with LPS (100 ng/ml) for the indicated time points and IκB degradation was measured by western blotting (FIG. 2B). TLR14 siRNA knockdown significantly reduced LPS-induced IκB degradation. FIGS. 2(A) and 2(B) represent two separate experiments, FIG. 3 shows the effect of TLR14 siRNA upon LPS induced p38 phosphorylation in U373 astrocytoma cells. U373s were transfected with either siRNA specific to TLR14 (Qiagen) or a non targeting siRNA as a negative control to ensure that the siRNA to TLR14 was specific. Cells were treated with LPS (100 ng/ml) for the indicated time points and p38 phosphorylation was measured by western blotting. TLR14 siRNA knockdown decreased phosphorylation of p38, FIG. 4 shows the binding of LPS with TLR14 in HEK293 TLR14-transfected cells. HEK293 cells were transfected with TLR14. After 24 hours, the cells were lysed and incubated with biotinylated LPS (1 µg/ml) alone or together with unlabeled LPS for 1 hour at room temperature. The lysates were then incubated with streptavidin agarose for a further hour before being washed and analysed by western blotting. In FIG. 4($a$), a 5-fold excess of unlabeled LPS has been included. In FIG. 4($b$), a 25-fold and 50-fold excess of unlabeled LPS has been included in the control samples, FIGS. 5A-5C show the knockdown of TLR14 marginally inhibits IκB degradation in response to LPS. Knockdown of TLR14 marginally inhibits IκB degradation in response to LPS after 30 sec. exposure (FIG. 5B) and after 2 min. exposure (FIG. 5C), FIGS. 6A-6B show the knockdown of TLR14 causes a decrease in IL-6 production and TNF-a cytokine production from THP1 cells. Knockdown of TLR14 causes a decrease in TNF-α (FIG. 6A) and IL-6 (FIG. 6B) cytokine production from THP1 cells, FIG. 7 shows a western blot of cytosol and membrane fractions, T indicates a transfected cell, while NT denotes a non-transfected cell, FIG. 8 shows western blot analysis showing expression of TLR14 in the brain of mice, FIG. 9 shows the localisation of endogenous TLR14 in THP1 cells. Membrane, cytosolic and whole cell extracts were prepared by Dounce homogenisation and ultracentrifugation. The samples were then tested for TLR14 expression using SDS-PAGE and western blotting, FIG. 10 shown the amino acid sequence of human Toll-like Receptor 14 which is defined as SEQ ID NO:1, FIG. 11 shows the amino acid sequence of a predicted soluble form of Toll-like Receptor 14, which is defined as SEQ ID NO:2, FIG. 12 shows the amino acid sequence of the murine form of Toll-like Receptor 14, which is defined as SEQ ID NO:3, and FIG. 13 shows the amino acid sequence of human Toll-like Receptor 4, which is defined as SEQ ID NO:4.

DETAILED DESCRIPTION OF THE INVENTION

Toll-like Receptor 14 (TLR14), is a leucine rich repeat containing protein, the human form of which comprises the amino acid sequence of SEQ ID NO:1 as shown below.

SEQ ID NO: 1
MEAARALRLLLVVCGCLALPPLAEPVCPERCDCQHPQHLLCTNRGLRVVP

KTSSLPSPHDVLTYSLGGNFITNITAFDFHRLGQLRRLDLQYNQIRSLHP

KTFEKLSRLEELYLGNNLLQALAPGTLAPLRKLRILYANGNEISRLSRGS

FEGLESLVKLRLDGNALGALPDAVFAPLGNLLYLHLESNRIRFLGKNAFA

QLGKLRFLNLSANELQPSLRHAATFAPLRSLSSLILSANSLQHLGPRIFQ

HLPRLGLLSLRGNQLTHLAPEAFWGLEALRELRLEGNRLSQLPTALLEPL

HSLEALDLSGNELSALHPATFGHLGRLRELSLRNNALSALSGDIFAASPA

LYRLDLDGNGWTCDCRLRGLKRWMGDWHSQGRLLTVFVQCRHPPALRGKY

-continued

LDYLDDQQLQNGSCADPSPSASLTADRRRQPLPTAAGEEMTPPAGLAEEL

PPQPQLQQQGRFLAGVAWDGAARELVGNRSALRLSRRGPGLQQPSPSVAA

AAGPAPQSLDLHKKPQRGRPTRADPALAEPTPTASPGSAPSPAGDPWQRA

TKHRLGTEHQERAAQSDGGAGLPPLVSDPCDFNKFILCNLTVEAVGADSA

SVRWAVREHRSPRPLGGARFRLLFDRFGQQPKFHRFVYLPESSDSATLRE

LRGDTPYLVCVEGVLGGRVCPVAPRDHCAGLVTLPEAGSRGGVDYQLLTL

ALLTVNALLVLLALAAWASRWLRRKLRARRKGGAPVHVRHMYSTRRPLRS

MGTGVSADFSGFQSHRPRTTVCALSEADLIEFPCDRFMDSAGGGAGGSLR

REDRLLQRFAD

The amino acid sequence of a predicted soluble form of Toll-like Receptor 14 is provided as SEQ ID NO:2.

SEQ ID NO: 2
MEAARALRLLLVVCGCLALPPLAEPVCPERCDCQHPQHLLCTNRGLRV

VPKTSSLPSPHDVLTYSLGGNFITNITAFDFHRLGQLRRLDLQYNQIR

SLHPKTFEKLSRLEELYLGNNLLQALAPGTLAPLRKLRILYANGNEIS

RLSRGSFEGLESLVKLRLDGNALGALPDAVFAPLGNLLYLHLESNRIR

FLGKNAFAQLGKLRFLNLSANELQPSLRHAATFAPLRSLSSLILSANS

LQHLGPRIFQHLPRLGLLSLRGNQLTHLAPEAFWGLEALRELRLEGNR

LSQLPTALLEPLHSLEALDLSGNELSALHPATFGHLGRLRELSLRNNA

LSALSGDIFAASPALYRLDLDGNGWTCDCRLRGLKRWMGDWHSQGRLL

TVFVQCRHPPALRGKYLDYLDDQQLQNGSCADPSPSASLTADRRRQPL

PTAAGEEMTPPAGLAEELPPQPQLQQQGRFLAGVAWDGAARELVGNRS

ALRLSRRGPGLQQPSPSVAAAAGPAPQSLDLHKKPQRGRPTRADPALA

EPTPTASPGSAPSPAGDPWQRATKHRLGTEHQERAAQSDGGAGLPPLV

SDPCDFNKFILCNLTVEAVGADSASVRWAVREHRSPRPLGGARFRLLF

DRFGQQPKFHRFVYLPESSDSATLRELRGDTPYLVCVEGVLGGRVCPV

APRDHCAGLVTLPEAGSRGGVDYQL

The amino acid sequence of the murine form of Toll-like Receptor 14 has also been defined. This is shown below as SEQ ID NO:3:

SEQ ID NO 3:
MEGVGAVRFWLVVCGCLAFPPRAESVCPERCDCQHPQHLLCTNRGLRAVP

KTSSLPSPQDVLTYSLGGNFITNITAFDFHRLGQLRRLDLQYNQIRSLHP

KTFEKLSRLEELYLGNNLLQALVPGTLAPLRKLRILYANGNEIGRLSRGS

FEGLESLVKLRLDGNVLGALPDAVFAPLGNLLYLHLESNRIRFLGKNAFS

QLGKLRFLNLSANELQPSLRHAATFVPLRSLSTLILSANSLQHLGPRVFQ

HLPRLGLLSLSGNQLTHLAPEAFWGLEALRELRLEGNRLNQLPLTLLEPL

HSLEALDLSGNELSALHPATFGHQGRLRELSLRDNALSALSGDIFAASPA

LYRLDLDGNGWTCDCRLRGLKRWMGNWHSQGRLLTVFVQCRHPPALRGKY

LDYLDDQLLQNGSCVDPSPSPTAGSRQWPLPTSSEEGMTPPAGLSQELPL

QPQPQPQQRGRLLPGVAWGGAAKELVGNRSALRLSRRGPGPHQGPSAAAP

GSAPQSLDLHEKPGRGRHTRANLSQTEPTPTSEPASGTPSARDSWQRAAK

QRLASEQQESAVQSVSGVGLPPLVSDPCDFNKFILCNLTVEAVSANSASV

RWAVREHRSPRPQGGARFRLLFDRFGQQPKFQRFVYLPERSDSATLHELR

GDTPYLVCVEGVLGGRVCPVAPRDHCAGLVTLPEAGGRGGVDYQLLTLVL

LAVNALLVLLALAAWGSRWLRRKLRARRKGGAPVHVRHMYSTRRPLRSMG

TGVSADFSGFQSHRPRTTVCALSEADLIEFPCDRFMDSTGGGTSGSLRRE

DHLLQRFAD

In certain embodiments of the present invention, it may be appropriate to substitute the human form of Toll-like Receptor 14 as defined in SEQ ID NO:1, with the murine form of Toll-like Receptor 14 as defined in SEQ ID NO:3.

TLR14, as defined in SEQ ID NO:1, contains 12 leucine rich repeats, a signal sequence and a putative transmembrane domain. Expression of TLR14 is seen in the brain, lung and ovary. The expression of TLR14 is enhanced by microbial products, such as LPS.

The inventors have identified that overexpression of TLR14 enhances LPS induced signalling, and accordingly, that there is upregulation of activation of the transcription factors NF-kB and IFN-regulated factor-3 (IRF3). LPS signalling, which is mediated through TLR4, also results in activate of mitogen-activated protein kinases (MAPKs), p38, c-jun, N terminal kinase (JNK) and p42/44.

Toll-like Receptor 14 has been surprisingly identified by the inventors as acting as a co-receptor with TLR4. This predicted function for TLR14 is proposed by the inventors who, without wishing to be bound by theory, have identified that; (i) transient expression of TLR14 enhances LPS signalling, (ii) knockdown of TLR14 with siRNA inhibits LPS signalling, (iii) LPS binds to TLR14, and (iv) TLR14 is expressed in membrane fractions, and also in the brain, wherein the expression levels of TLR14 are seen to be enhanced during inflammation in an EAE mouse model, suggesting that TLR14 may be upregulated in certain disease and inflammatory conditions.

Again, without wishing to be bound by theory, the inventors predict that the involvement of TLR14 in endotoxin-mediated signalling results from TLR14 complexing with endotoxin, such as LPS. TLR14 associates with TLR4 as a co-receptor. TLR4 does not bind to endotoxin directly. Rather, MD-2 interacts with the endotoxin, this producing TLR4/MD-2 complexes which produce TLR4 dependent cell stimulation. In this role, TLR14 functions in a manner similar to CD14, which is also known to exist as both a membrane bound and soluble form. Accordingly, LPS is transferred from TLR14 to a pre-formed complex of TLR4 and MD-2. The binding of LPS to the TLR4/MD-2 complex results in TLR4 activation by the PAMP LPS, and in turn downstream signalling which originates from the TLR4 TIR domain. The inventors have observed that although TLR14 and CD14 share a very low level of sequence homology, they exhibit structural homology. For example, CD14 exhibits a series of leucine-rich repeats, this series of leucine-rich repeats also being evident in the structure of TLR14. Further, CD14 has the same solenoid structure found in the ectodomain of Toll-like Receptors. CD14 differs from Toll-like Receptors in that it does not have a TIR signalling domain.

The amino sequence of the human Toll-like Receptor 4 (TLR4) protein has been previously defined and this shown below as SEQ ID NO:4.

SEQ ID NO: 4:
MELNFYKIPDNLPFSTKNLDLSFNPLRHLGSYSFFSFPELQVLDLSRCEI

QTIEDGAYQSLSHLSTLILTGNPIQSLALGAFSGLSSLQKLVAVETNLAS

LENFPIGHLKTLKELNVAHNLIQSFKLPEYFSNLTNLEHLDLSSNKIQSI

YCTDLRVLHQMPLLNLSLDLSLNPMNFIQPGAFKEIRLHKLTLRNNFDSL

NVMKTCIQGLAGLEVHRLVLGEFRNEGNLEKFDKSALEGLCNLTIEEFRL

AYLDYYLDDIIDLFNCLTNVSSFSLVSVTIERVKDFSYNFGWQHLELVNC

KFGQFPTLKLKSLKRLTFTSNKGGNAFSEVDLPSLEFLDLSRNGLSFKGC

CSQSDFGTTSLKYLDLSFNGVITMSSNFLGLEQLEHLDFQHSNLKQMSEF

SVFLSLRNLIYLDISHTHTRVAFNGIFNGLSSLEVLKMAGNSFQENFLPD

IFTELRNLTFLDLSQCQLEQLSPTAFNSLSSLQVLNMSHNNFFSLDTFPY

KCLNSLQVLDYSLNHIMTSKKQELQHFPSSLAFLNLTQNDFACTCEHQSF

LQWIKDQRQLLVEVERMECATPSDKQGMPVLSLNITCQMNKTIIGVSVLS

VLVVSVVAVLVYKFYFHLMLLAGCIKYGRGENIYDAFVIYSSQDEDWVRN

ELVKNLEEGVPPFQLCLHYRDFIPGVAIAANIIHEGFHKSRKVIVVVSQH

FIQSRWCIFEYEIAQTWQFLSSRAGIIFIVLQKVEKTLLRQQVELYRLLS

RNTYLEWEDSVLGRHIFWRRLRKALLDGKSWNPEGTVGTGCNWQEATSI

In providing various assay methods which allow for the identification of modulatory compounds which inhibit the association of TLR14 with TLR4 as a co-receptor, the invention provides a means to inhibit, suppress or downregulate signalling which is mediated by TLR4 which may result in an aberrant immune response. Such TLR4-mediated signalling is causative of the condition sepsis, this resulting following the binding to TLR4 of LPS.

The invention further provides for modulatory compounds which have utility in suppressing TLR4 mediated immune responses, and in particular those mediated in response to LPS.

Antibodies and Related Binding Compounds

In certain embodiments, the invention extends to the use of antibodies and related binding compounds for the inhibition of biological functional activity of TLR14, for example due to preventing the binding of endotoxin, such as LPS, to TLR14, or due to the antibody preventing the complexing of TLR14 and TLR4 to form a co-receptor complex.

In certain embodiments, the compound which inhibits the biological function of TLR14 is an antibody or a binding compound which is derived from an antibody.

An "antibody" is an immunoglobulin, whether naturally derived or partly or wholly synthetically produced. The term also covers any polypeptide, protein or peptide having a binding domain that is, or is homologous in function to, an antibody binding domain. Said polypeptides or proteins can be derived from natural sources, or they may be partly or wholly synthetically produced. Examples of antibodies are the immunoglobulin isotypes, for example IgG, IgA, IgM, IgE and the like as well as their isotypic subclasses, for example, IgG1, IgG2 and IgG3. The term further extends to antibody fragments which comprise an antigen binding domain and therefore exhibit binding specificity, such as Fab, F(ab')2, scFv, Fv, dAb, Fd, fragments and bi-specific antibodies.

In various embodiments, the antibody for use in the invention may be a polyclonal antibody, a chimeric antibody, or a synthesized or synthetic antibody. In certain embodiments, the antibody may be a Camelid antibody, in particular a Camelid heavy chain antibody. Further, the antibody fragment may be a domain antibody or a nanobody derived from a Camelid heavy chain antibody. In certain embodiments the antibody may be a shark antibody or a shark derived antibody.

In certain embodiments, the antibody is an "isolated antibody", this meaning that the antibody is (1) free of at least some proteins with which it would normally be found, (2) is essentially free of other proteins from the same source, e.g., from the same species, (3) is expressed by a cell from a different species, or (4) does not occur in nature.

As antibodies can be modified in a number of ways, the term "antibody" should be construed as covering any binding member or substance having a binding domain with the required specificity. The antibody of the invention may be a monoclonal antibody, or a fragment, derivative, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in European Patent Application Publication Number EP 0,120,694 and European Patent Application Publication Number EP 0,125,023.

The constant region of the antibody may be of any suitable immunoglobulin subtype, however it is preferred that the antibody subtype is IgG1. However, in alternative embodiments, the subtype of the antibody may be of the class IgA, IgM, IgD and IgE where a human immunoglobulin molecule is used. Such an antibody may further belong to any subclass e.g. IgG1, IgG2a, IgG2b, IgG3 and IgG4.

Fragments of a whole antibody can perform the function of antigen binding. Examples of such binding fragments are; a Fab fragment comprising of the VL, VH, CL and CH1 antibody domains; an Fv fragment consisting of the VL and VH domains of a single antibody; a F(ab')2 fragments, a bivalent fragment comprising two linked Fab fragments; a single chain Fv molecule (scFv), wherein a VH domain and a VL domain are linked by a peptide linker which allows the two domains to associate to form an antigen binding site; or a bi-specific antibody, which may be multivalent or multispecific fragments constructed by gene fusion.

A fragment of an antibody or of a polypeptide for use in the present invention, for example, a fragment of a TLR14 or TLR4 specific antibody (the latter in the case of an antibody which inhibits TLR14 biological function by binding to TLR4 at an epitope which prevents TLR14 complexing with TLR4 as a co-receptor), generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

A "derivative" of such an antibody or polypeptide, or of a fragment of a TLR14 or TLR4 specific antibody means an antibody or polypeptide modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having TLR14 and/or TLR4 binding activity. Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

The antibodies for use in the binding assays of the present invention may be provided by a number of techniques. For example, a combinatorial screening technique such as a phage display-based biopanning assay may be used in order to identify amino acid sequences which have binding specificity to binding epitopes present on TLR14 or TLR4. Such phage display biopanning techniques involve the use of phage display libraries, which are utilised in methods which identify suitable epitope binding ligands in a procedure which mimics immune selection, through the display of antibody binding fragments on the surface of filamentous bacteria. Phage with specific binding activity are selected. The selected phage can thereafter be used in the production of chimeric, CDR-grafted, humanised or human antibodies.

In certain embodiments, the antibody is a monoclonal antibody, which may be produced using any suitable method which produces antibody molecules by continuous cell lines in culture. Suitable methods will be well known to the person skilled in the art and include, for example, the method of Kohler and Milstein (Kohler et al. Nature, 256, 495-497. 1975). Chimeric antibodies or CDR-grafted antibodies are further provided within the scope of the present invention. In certain embodiments, the antibodies of the invention may be produced by the expression of recombinant DNA in host cell.

In certain embodiments, the monoclonal antibodies may be human antibodies, produced using transgenic animals, for example, transgenic mice, which have been genetically modified to delete or suppress the expression of endogenous murine immunoglobulin genes, with loci encoding for human heavy and light chains being expressed in preference, this resulting in the production of fully human antibodies.

In certain embodiments the antibodies may be humanized antibodies. Humanized antibodies may be produced, for example, by the method of Winter as described in U.S. Pat. No. 5,585,089. A humanised antibody may be a modified antibody having the hypervariable region of a monoclonal antibody such as a TLR14 or TLR4 specific antibody and the constant region of a human antibody. Thus the binding member may comprise a human constant region. The variable region other than the hypervariable region may also be derived from the variable region of a human antibody and/or may also be derived from a monoclonal antibody such as a TLR14 or TLR4 specific antibody. In such case, the entire variable region may be derived from the murine monoclonal antibody and the antibody is said to be chimerised. Methods for making chimeric antibodies are known in the art. Such methods include, for example, those described in U.S. Pat. Nos. 4,816,397 and 4,816,567, of Boss and Cabilly respectively.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, European Patent Application No 0,184,187, GB Patent Application No. 2,188,638A or European Patent Application No. 0,239,400. A hybridoma or other cell producing an antibody may be subject to genetic mutation or other changes, which may or may not alter the binding specificity of antibodies produced.

In certain embodiments, where the TLR14 inhibitory compound is an antibody, the antibody is administered to a subject in a therapeutically effective amount. In certain embodiments, the therapeutically effective amount comprises the antibody in a range chosen from 1 µg/kg to 20 mg/kg, 1 g/kg to 10 mg/kg, 1 µg/kg to 1 mg/kg, 10 µg/kg to 1 mg/kg, 10 µg/kg to 100 µg/kg and 500 µg/kg to 1 mg/kg.

Production of Antibodies

Certain methodologies for producing antibodies which have an affinity and binding specificity for an epitope present on TLR14 or TLR4 which restricts TLR14 functional activity are described hereinbefore.

The antibodies or antibody fragments of and for use in the present invention may also be generated wholly or partly by chemical synthesis. The antibodies can be readily prepared according to well-established, standard liquid or, preferably, solid-phase peptide synthesis methods, general descriptions of which are broadly available and are well known by the person skilled in the art. Further, they may be prepared in solution, by the liquid phase method or by any combination of solid-phase, liquid phase and solution chemistry.

Another convenient way of producing antibodies or antibody fragments suitable for use in the present invention is to express nucleic acid encoding them, by use of nucleic acid in an expression system.

Nucleic acid for use in accordance with the present invention may comprise DNA or RNA and may be wholly or partially synthetic. In a preferred aspect, nucleic acid for use in the invention codes for antibodies or antibody fragments of the invention as defined above. The skilled person will be able to determine substitutions, deletions and/or additions to such nucleic acids which will still provide an antibody or antibody fragment of the present invention.

Nucleic acid sequences encoding antibodies or antibody fragments for use with the present invention can be readily prepared by the skilled person using the information and references contained herein and techniques known in the art (for example, see Sambrook et al. (1989), and Ausubel et a.l, (1992)), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells, NSO mouse myeloma cells. A common, preferred bacterial host is *E. coli*. The expression of antibodies and antibody fragments in prokaryotic cells such as *E. coli* is well established in the art. Expression in eukaryotic cells in culture is also available to those skilled in the art as an option for production of a binding member.

General techniques for the production of antibodies are well known to the person skilled in the field, with such methods being discussed in, for example, Kohler and Milstein (1975) Nature 256: 495-497; U.S. Pat. No. 4,376,110; Harlow and Lane, Antibodies: a Laboratory Manual, (1988) Cold Spring Harbor, the contents of which are incorporated herein by reference.

Techniques for the preparation of recombinant antibody molecules are described in the above references and also in, for example, EP 0623679 and EP 0368684, which are incorporated herein by reference.

In certain embodiments of the invention, recombinant nucleic acids comprising an insert coding for a heavy chain variable domain and/or for a light chain variable domain of antibodies are employed. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

Recombinant DNA technology may be used to improve the antibodies of the invention. Thus, chimeric antibodies may be constructed in order to decrease the immunogenicity thereof in diagnostic or therapeutic applications. Moreover, immunogenicity within, for example, a transgenic organism such as a pig, may be minimised, by altering the antibodies by CDR grafting in a technique analogous to humanising antibodies. Examples of such techniques are described in EP 0,239,400 to Winter.

In order to reduce immunogenicity within a recipient, the invention may employ recombinant nucleic acids comprising an insert coding for a heavy chain variable domain of an antibody fused to a human constant domain. Likewise the invention concerns recombinant DNAs comprising an insert coding for a light chain variable domain of an antibody fused to a human constant domain kappa or lambda region.

Antibodies may also be generated by mutagenesis of antibody genes to produce artificial repertoires of antibodies. This technique allows the preparation of antibody libraries. Antibody libraries are also available commercially. Hence, the present invention advantageously employs artificial repertoires of immunoglobulins, preferably artificial scFv repertoires, as an immunoglobulin source in order to identify binding molecules which have specificity for TLR14 or TLR4.

Antibody Selection Systems

Immunoglobulins which are able to bind to TLR14 or TLR4 and inhibit TLR14 biological function, and which accordingly may be used in the methods of the invention, can be identified using any technique known to the skilled person. Such immunoglobulins may be conveniently isolated from libraries comprising artificial repertoires of immunoglobulin polypeptides. A "repertoire" refers to a set of molecules generated by random, semi-random or directed variation of one or more template molecules, at the nucleic acid level, in order to provide a multiplicity of binding specificities. Methods for generating repertoires are well characterised in the art.

Any library selection system may be used in conjunction with the invention. Selection protocols for isolating desired members of large libraries are known in the art, as typified by phage display techniques. Such systems, in which diverse peptide sequences are displayed on the surface of filamentous bacteriophage, have proven useful for creating libraries of antibody fragments (and the nucleotide sequences that encode them) for the in-vitro selection and amplification of specific antibody fragments that bind a target antigen. The nucleotide sequences encoding the VH and VL regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phage bodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straight forward.

Methods for the construction of bacteriophage antibody display libraries and lambda phage expression libraries are well known in the art (for example, McCafferty et al. (1990) Nature 348 552-554. One particularly advantageous approach has been the use of scFv phage-libraries (see for example Huston et al., 1988, Proc. Natl. Acad. Sci. USA).

An alternative to the use of phage or other cloned libraries is to use nucleic acid, preferably RNA, derived from the B cells of an animal which has been immunised with the selected target, e.g. the TLR2 epitope of the present invention.

Isolation of V-region and C-region mRNA permits antibody fragments, such as Fab or Fv, to be expressed intracellularly. Briefly, RNA is isolated from the B cells of an immunised animal, for example from the spleen of an immunised mouse or the circulating B cells of a llama, and PCR primers used to amplify VH and VL cDNA selectively from the RNA pool. The VH and VL sequences thus obtained are joined to make scFv antibodies. PCR primer sequences may be based on published VH and VL sequences.

Peptidomimetics

Peptide analogues, such as peptidomimetics or peptide mimetics are non-peptide compounds with properties representative of a template peptide. Such peptide analogues are typically developed using computerised molecular modelling. Peptidomimetics which are structurally similar to peptides which have affinity and binding specificity to TLR14 and which inhibit the biological functional activity of TLR14 in binding endotoxin, such as LPS and associating with TLR4 as a co-receptor complex may be used to mediate similar prophylactic and therapeutic effects to polypeptides and proteins which are determined to have such TLR14 inhibitory function.

Peptidomimetics are typically structurally similar to a template peptide, but have one or more peptide linkages replaced by an alternative linkage, by methods which are well known in the art. For example, a peptide which has a binding specificity to a TLR14 epitope may be modified such that it comprises amide bond replacement, incorporation of non peptide moieties, or backbone cyclisation. Suitably if cysteine is present the thiol of this residue is capped to prevent damage of the free sulphate group. A peptide may further be modified from the natural sequence to protect the peptides from protease attack.

Suitably a peptide use as a TLR14 inhibitory compound in the present invention may be further modified using at least one of C and/or N-terminal capping, and/or cysteine residue capping. Furthermore, a peptide for use in the present invention may be capped at the N terminal residue with an acetyl group. Suitably, a peptide of and for use in the present invention may be capped at the C terminal with an amide group. Suitably, the thiol groups of cysteines are capped with acetamido methyl groups.

Combinatorial Library

Combinatorial library technology (Schultz, J S (1996) Biotechnol. Prog. 12:729-743) provides an efficient way of testing a potentially vast number of different substances for ability to modulate activity of a polypeptide, this case, the biological activity of TLR14. Prior to, or as well as being screened for, modulation of activity, test compounds may be screened for their ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide.

The amount of test substance or compound which may be added to an assay of the invention will normally be determined by trial and error depending upon the type of compound used. Typically, from about 0.01 to 100 nM concentrations of putative inhibitor compound may be used, for example from 0.1 to 10 nM. Greater concentrations may be used when a peptide is the test substance.

Production of Inhibitory Polypeptides

In certain further aspects, the compound which inhibits the biological function of TLR14 in binding LPS and complexing with TLR4 is a polypeptide. Expression, isolation and purification of suitable polypeptides may be accomplished by any suitable technique.

A method for producing polypeptides comprises culturing host cells transformed with a recombinant expression vector encoding a polypeptide under conditions that promote expression of the polypeptide, then recovering the expressed polypeptides from the culture. The person skilled in the art will recognise that the procedure for purifying the expressed polypeptides will vary according to such factors as the type of host cells employed, and whether the polypeptide is intracellular, membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, avian, microbial, viral, bacterial, or insect gene. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired (E. coli) host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide during translation, but allows secretion of polypeptide from the cell.

Suitable host cells for expression of polypeptides include higher eukaryotic cells and yeast. Prokaryotic systems are also suitable. Mammalian cells, and in particular CHO cells are particularly preferred for use as host cells. Appropriate cloning and expression vectors for use with mammalian, prokaryotic, yeast, fungal and insect cellular hosts are described, for example, in Pouwels et al. Cloning Vectors: A Laboratory Manual, Elsevier, N.Y., (1986) (ISBN 0444904018).

Small Molecules

In certain further embodiments, the compound which inhibits the biological function of TLR14 may be a small molecule.

Non-peptide "small molecules" are often preferred for many in-vivo pharmaceutical uses. Accordingly, a mimetic or mimic of a compound which is identified according to any one of the assay methods of the present invention as inhibiting TLR14 expression or biological function may be designed for pharmaceutical uses. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been determined, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can also be used in this modelling process.

In a variant of this approach, the three-dimensional structure of the ligand and its binding partner are modelled. This can be especially useful where the ligand and/or binding partner change conformation on binding, allowing the model to take account of the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in-vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in-vivo or clinical testing.

Inhibitory Nucleic Acids Molecules

The invention extends to methods of suppressing endotoxin-mediated TLR4-mediated signalling, by administering compounds or compositions which suppress the expression of the TLR14 gene product.

Suppression of expression of TLR14 may be achieved using a number of techniques which will be well known to the person of ordinary skill in the art. For example, suppression may be mediated by an inhibitory nucleic acid selected from the group comprising, but not limited to: an anti-sense oligonucleotide, anti-sense DNA, anti-sense RNA, ribozyme, iRNA, miRNA, sRNA, shRNA.

As such, in certain further aspects, the present invention extends to a method for the treatment and/or prophylaxis of a TLR4-mediated inflammatory condition by administering to a subject a therapeutically effective amount of an inhibitory nucleic acid which blocks the expression of Toll-like Receptor 14.

As herein defined, the terms "blocks" and "blocking" when used in relation to TLR14 gene expression mean silencing the expression of at least one gene which results in the expression of the Toll-like Receptor 14 protein. Gene silencing is the switching off of the expression of a gene by a mechanism other than genetic modification. Gene silencing can be mediated at the transcriptional level or at the post-transcriptional level. Transcriptional gene silencing can results in a gene being inaccessible to transcriptional machinery, and can be mediated, for example, by means of histone modifications. Post-transcriptional gene silencing results from the mRNA of a gene being destroyed, thus preventing an active gene product, such as a protein, in the present case the TLR-14 protein.

Accordingly, the invention further extends to the administration to a subject of an effective amount of an inhibitory nucleic acid molecule, such as an RNAi (RNA interference) agent, for example an interfering ribonucleic acid (such as siRNA or shRNA) or a transcription template thereof, such as a DNA encoding an shRNA to at least one cell type, tissue or organ present in the subject in order to block the expression of the TLR14 protein.

In certain further embodiments, the inhibitory nucleic acid molecule may be an antisense RNA molecule. Antisense causes suppression of gene expression and involves single stranded RNA fragments which physically bind to mRNA, this blocking mRNA translation.

Techniques for the preparation of appropriate nucleic acid for use as inhibiting nucleic acids are well known to the person skilled in the art and are discussed further hereinafter.

According to a further aspect of the invention there is provided the use of an inhibitory nucleic acid which blocks the expression of the Toll-like Receptor 14 protein in the preparation of a medicament for the treatment and/or prophylaxis of a TLR4-mediated inflammatory condition. In certain embodiments, the TLR4-mediated inflammatory condition is sepsis.

Various aspects of the present invention provide for the use of inhibiting nucleic acids for the silencing of TLR14 gene expression.

Double-stranded RNA induces potent and specific gene silencing through a process referred to as RNA interference (RNAi) or post transcriptional gene silencing (PTGS). RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger.

RNAi has become the method of choice for loss-of-function investigations in numerous systems including mammalian cell lines. To specifically silence a gene in most mammalian cell lines, small interfering RNAs (siRNA) are used because large dsRNAs (>30 base pairs) trigger the interferon response and cause nonspecific gene silencing.

The RNAi agents employed in are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By "oligoribonucleotide", it is meant a ribonucleic acid that does not exceed about 100 nucleotides (nt) in length, and typically does not exceed about 75 nucleotides in length, where the length in certain embodiments is less than about 70 nucleotides. As described herein, the length of the duplex structures for use in the present invention can typically ranges from about 15 to 30 base pairs, more preferably from about 15 to 29 base pairs.

As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded (such as sense or antisense) and double-stranded polynucleotides.

The term "expression" with respect to a nucleic acid or gene sequence refers to transcription of a gene and, as appropriate, translation of the resulting mRNA transcript to a protein. Thus, as will be clear from the context, expression of a protein coding sequence results from transcription and translation of the coding sequence.

"Inhibition of gene expression" refers to the absence (or observable decrease) in the level of protein and/or mRNA product from a target gene. "Specificity" refers to the ability to inhibit the target gene without manifest effects on other genes of the cell. Confirmation of inhibiting can be obtained through the use of techniques which are well known to the person skilled in the art such as: Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed.

Depending on the assay, quantitation of the amount of TLR14 gene expression allows one to determine a degree of inhibition which is greater than 10%, 33%, 50%, 90%, 95% or 99% as compared to a cell not treated according to the present invention. Lower doses of administered active agent and longer times after administration of active agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

RNAi

Accordingly, as indicated above, one aspect of the present invention provides methods of employing RNAi to inhibit or suppress the expression of TLR14 in a suitable cell type. By the term "inhibiting expression", it is meant that the level of expression of the TLR14 gene or coding sequence is reduced or inhibited by at least about 2-fold, usually by at least about 5-fold, e.g., 10-fold, 15-fold, 20-fold, 50-fold, 100-fold or more, as compared to a control. In certain embodiments, the expression of the TLR14 target gene is reduced to such an extent that expression of the target TLR14 gene/coding sequence is effectively inhibited. In this regard, inhibiting expression of a target gene means inhibiting the transcription or translation of a coding sequence such as genomic DNA, mRNA etc., into a polypeptide product such as a protein, in the present case, TLR14.

In certain embodiments, instead of the RNAi agent being an interfering ribonucleic acid, such as an siRNA or shRNA as described above, the RNAi agent may encode an interfering ribonucleic acid, for example an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, such as a plasmid vector, a viral vector.

Administration of the RNAi agent to the TLR14 expressing cell may be effected by means of a viral vector, or by other protocols which will be known to the person of ordinary skill in the art. For example, the nucleic acids may be introduced into the cell by way of microinjection, or by the fusion of vesicles. For example, the RNAi agent can be directly injected into the target cell. The agent may be introduced in an amount which allows delivery of at least one copy per cell. Higher doses (e.g., at least 5, 10, 100, 500 or 1000 copies per cell) of the agent may yield more effective inhibition; lower doses may also be useful for specific applications.

Antisense

Also provided by the present invention are antisense nucleic acids for use in the silencing of the expression of TLR14. The antisense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted TLR14 gene, and inhibits expression of the targeted TLR14 gene product.

Antisense molecules inhibit gene expression through various mechanisms, for example by reducing the amount of mRNA available for translation, through activation of RNAse H, or steric hindrance. One or a combination of antisense molecules may be administered, where a combination may comprise multiple different sequences. Antisense molecules may be produced by expression of all or a part of the target TLR14 gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 16 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), Nature Biotechnol. 14:840-844).

Antisense oligonucleotides may be chemically synthesized by methods known in the art (see Wagner et al. (1993), supra, and Milligan et al., supra). Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Soluble Proteins

In certain further embodiments the compounds which inhibit Toll-like Receptor 14 biological function is a soluble protein, typically a soluble form of TLR14.

Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

The amino acid sequent of SEQ ID NO:2, as defined herein, shows the amino acid sequence of the TLR14 sequence defined in SEQ ID NO:1 in soluble form, wherein the predicted transmembrane domain and C-terminal terminus are removed. This soluble form of Toll-like Receptor 14 may function to suppress the biological function of membrane bound Toll-like Receptor 14 by competitively binding with LPS, this resulting in a reduction in membrane bound TLR14 which is associated with LPS, and hence, in turn, a reduction in LPS-mediated activation of Toll-like Receptor 4, as the inventors predict that soluble forms of TLR14 which are associated with endotoxin, such as LPS, will not complex with TLR4 as a co-receptor.

In certain embodiments, the soluble form of TLR14 may be provided as a fusion protein. In certain embodiments, said fusion protein is comprised of a soluble portion of the TLR14 receptor, typically the extracellular domain or a portion thereof, for example having the amino acid sequence of SEQ ID NO:2, conjoined to a secondary peptide. In certain embodiments, the secondary peptide is derived from an immunoglobulin, and is typically the Fc receptor binding protein derived from the heavy chain of an immunoglobulin, typically a human immunoglobulin. The inclusion of the Fc domain in the fusion protein prolongs the circulatory half-life of the therapeutic protein.

The soluble TLR14 amino acid sequence and the immunoglobulin Fc receptor binding portion may be joined by any suitable technique, but are typically linked by a covalent bond. However a non-covalent bond may also be used. Alternatively, the polypeptide sequences could be directly conjoined or could be joined by means of a linkage moiety or spacer. A linker moiety such as a hinge region derived from an immunoglobulin may be used. The hinge region serves not only to link the amino acid defining the antigenic polypeptide with the amino acid defining the FcR binding polypeptide of the immunoconjugate, but also provides increased flexibility of the immunoconjugate which can confer improved binding specificity. Typically, the linker acts primarily as a spacer. Typically the linker is comprised of amino acids linked together by peptide bonds. The linker may, for example, comprise from 1 to 20 amino acids. Suitably the linker may comprise amino acid residues which are sterically unhindered, such as glycine and alanine. Suitable forms of linker moieties, are described hereinafter.

The amino acid defining the antigenic fragment of the immunoconjugate may be linked to the linker moiety at either its N-(amino) or C-(carboxyl). Suitable conjugation and linkage techniques would be well known to those skilled in the art and may include, for example, conjugation by thio-ester crosslinking utilising cysteine residues of the Fc polypeptide. Alternatively, the conjugation can involve the use of chemical crosslinking molecules, such as the use of heterobifunctional crosslinking agents, such as succinimidyl esters, for example, 3-(2-pyridyldithio)propionate or succinimidyl acetylthioacetate (Molecular Probes Inc. Handbook, Chapter 5, section 5.3).

Further techniques which may have utility in the conjugation of the antigenic fragment to the Fc binding polypeptide would include the techniques described in published International Patent Applications No WO 94/04690 and WO 96/27011.

Conjugation may further be achieved by genetic means through the use of recombinant DNA techniques that are well know in the art, such as those set forth in the teachings of Sambrook et al. Molecular Cloning: A Laboratory Manual, 2 ed. Vol. 1, pp. 1.101-104, Cold Spring Harbor Laboratory Press, (1989) and F. M. Ausubel et al. Current Protocols in Molecular Biology, Eds. J. Wiley Press (2006), the relevant portions of which are incorporated herein by reference.

Combination Medicaments

As described hereinbefore, in certain aspects, the present invention extends to combinational therapies wherein compositions or methods relate to the administration of compounds which inhibit the biological functional activity of TLR14, and which are administered in combination with at least one further therapeutic compound which serves to suppress CD14 activity.

Typically the primary and secondary therapeutic compositions are given contemporaneously. In certain embodiments, the primary therapeutic composition (i.e. the compound which antagonises the functional activity of TLR14) and the secondary therapeutic compounds are administered simultaneously. In certain further embodiments, they are administered sequentially.

In certain embodiments, the combination therapy may comprise a TLR14 functional inhibitor, such as an antibody, a peptide, a small molecule or a peptidomimetic, which is co-administered to a subject along with at least one of: a CD14 inhibitor, a cytokine inhibitor (such as, but not limited to an inhibitor of IL-1, IL-6, IL-8 and IL-15), and inhibitor of tumour necrosis factor, a growth factor inhibitor, an immunosuppressor, an anti-inflammatory, an enzymatic inhibitor, a metabolic inhibitor, a cytotoxic agent or a cytostatic agent.

A person of relevant skill in the field will recognise that the administration to a subject of a combination therapy can be advantageous in that it permits administration of a lower dose of therapeutic to a subject in order to achieve and associated therapeutically effective effect. The administration of a lower combined dose also results in the subject being exposed to a lower toxicity level derived from the administered compound. Furthermore, as the secondary therapeutic compounds which are administered as part of the combination therapy provided by the invention target different pathways, there is likely to be a synergistic improvement in the overall efficacy of the therapy. An improvement in efficacy would again result in the need for a lower dose to be administered and as such an associated reduction in toxicity.

Secondary compounds for use in suppressing the biological functional activity of CD14 may include, but are not limited to; soluble forms of CD14, peptide inhibitor compounds, small molecule, fusion proteins or ligands, and antibodies.

Pharmaceutical Compositions

The present invention extends to a pharmaceutical composition comprising a compound which inhibits the expression or biological functional activity of TLR14. Pharmaceutical compositions according to and for use in accordance with the present invention may comprise, in addition to active ingredient (i.e. an inhibitor of TLR14 expression or biological activity), a pharmaceutically acceptable excipient, carrier, buffer stabiliser or other materials well known to those skilled in the art. Examples of suitable pharmaceutical carriers include; water, glycerol, ethanol and the like.

The monoclonal antibody or fusion protein of the present invention may be administered to a patient in need of treatment via any suitable route. As detailed herein, it is preferred that the composition is administered parenterally by injection or infusion. Examples of preferred routes for parenteral administration include, but are not limited to; intravenous, intracardial, intraarterial, intraperitoneal, intramuscular, intracavity, subcutaneous, transmucosal, inhalation or transdermal.

Routes of administration may further include topical and enteral, for example, mucosal (including pulmonary), oral, nasal, rectal.

The formulation may be a liquid, for example, a physiologic salt solution containing non-phosphate buffer at pH 6.8-7.6, or a lyophilised or freeze dried powder.

In certain embodiments, the composition is deliverable as an injectable composition. For intravenous, intradermal or subcutaneous application, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

Dosage regimens can include a single administration of the composition of the invention, or multiple administrative doses of the composition. The compositions can further be administered sequentially or separately with other therapeutics and medicaments which are used for the treatment of the condition for which the fusion protein of the present invention is being administered to treat.

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The nomenclature used to describe the polypeptide constituents of the fusion protein of the present invention follows the conventional practice wherein the amino group (N) is presented to the left and the carboxy group to the right of each amino acid residue.

The expression "amino acid" as used herein is intended to include both natural and synthetic amino acids, and both D and L amino acids. A synthetic amino acid also encompasses chemically modified amino acids, including, but not limited to salts, and amino acid derivatives such as amides. Amino acids present within the polypeptides of the present invention can be modified by methylation, amidation, acetylation or substitution with other chemical groups which can change the circulating half life without adversely affecting their biological activity.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived As used herein, the term "therapeutically effective amount" means the amount of an agent, binding compound, small molecule, fusion protein or peptidomimetic of the invention which is required to suppress a TLR4-mediated inflammatory condition.

As used herein, the term "prophylactically effective amount" relates to the amount of a composition which is required to prevent the initial onset, progression or recurrence of TLR4-mediated inflammatory condition, such as sepsis.

As used herein, the term "treatment" and associated terms such as "treat" and "treating" means the reduction of the progression, severity and/or duration of a TLR4 or TLR14 mediated condition or at least one symptom thereof, wherein said reduction or amelioration results from the administration of a compound which disrupts or prevents the association of TLR14 as a co-receptor with TLR4.

The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition.

As used herein, the term "subject" refers to an animal, preferably a mammal and in particular a human. In a particular embodiment, the subject is a mammal, in particular a human. The term "subject" is interchangeable with the term "patient" as used herein.

The following experimental techniques and protocols were used in the examples of the present invention.

Luciferase Reporter Assay

U373 cells were seeded into 96-well plates ($2 \times 10^4$ cells per well) and transfected the next day with empty vector or TLR14 expression vector (50 ng) and 80 ng of NF-KB-luciferase reporter gene (Stratagene) along with 40 ng of the *Renilla* luciferase internal control plasmid (Promega). GENEJUICE™ (Novagen) was used for transient transfection according to the manufacturer's instructions. After 24 hours, cells were stimulated for 6 hrs with LPS (Sigma) at a final concentration of 100 ng/ml. The cells were then harvested in passive lysis buffer (Promega) and reporter gene activity was measured in a luminometer. Data are expressed as mean fold induction ±s.d. relative to control levels, for a representative experiment from a minimum of three separate experiments, each performed in triplicate.

siRNA Based TLR14 Knockdown

Commercially available siRNA with binding specificity to TLR14 were obtained from Dharmacon and Qiagen. Human astrocytoma U373 cells were set up in 10 cm dishes at a concentration of $5 \times 10^4$ cells/ml. The following day the cells were transfected with siRNAs using OLIGOFECTAMINE™ (Invitrogen) according to the manufacturer's instructions. After 48 hours, the medium was removed from the cells and SDS-PAGE sample buffer was added directly to the plates. The samples were sonicated and boiled for 5 minutes before being centrifuged at 13000 rpm for 1 minute. The samples were then analysed by SDS-PAGE and western blotting. The antibodies to IkBa and phospho-p38 were obtained from Cell Signalling. The TLR4 antibody was obtained from Santa Cruz.

In the experiments involving THP1, the cells were transfected with siRNA specific to TLR14 (Qiagen) using the Amaxa based transfection system (program S-019). After 72 hours, knockdown of TLR14 was confirmed by western blotting. A scrambled version of the Qiagen siRNA was used as a negative control to ensure that the siRNA used was specific to TLR14. Cells were treated with 100 ng/ml LPS for the indicated time points and IkB degradation was measured by western blotting. For the experiments involving cytokine measurements, after 72 hours the cells were stimulated with 100 ng/ml LPS for 24 hours. Supernatants were removed and IL-6 and TNF-α ELISAs were performed.

LPS Binding Assays

HEK293 cells were seeded on 10 cm plates at $1 \times 10^5$ cells/ml. The following day, cells were transfected with 3 µg of TLR14 expression plasmid. After 24 hours the cells were lysed in 800 µl Hepes buffer containing 1% NP40. The cell lysates were incubated for 1 hr at room temperature with Biotin-LPS (Invivogen) at a final concentration of 1 µg/ml in the presence and absence of unlabeled LPS. Steptavidin-agarose beads (Pierce) were washed twice with PBS before being added to the samples (40 µl/point). After one hour the beads were washed ×3 with lysis buffer and resuspended with 20 µl of SDS-PAGE sample buffer. The protein samples were run on 10% SDS-PAGE gels and transferred to nitrocellulose for western blotting. The resulting blots were probed with anti-TLR14 antibody.

EXAMPLES

Example 1

TLR14 Involvement with LPS Signalling

Reporter gene assays were carried out in the LPS responsive astrocytoma cell line, U373, which were transfected with 50 ng of empty vector control or TLR14 plasmid for 24 hours. Cells were stimulated with LPS (100 ng/ml) for 6 hours in the presence or absence of over-expressed TLR14 before being harvested and analysed for reporter gene activity.

As is shown in FIG. 1, the presence of TLR14 enhanced LPS induced NF-κB reporter gene expression (shown in terms of an increase in fold stimulation) when compared to empty vector (denoted EV in FIG. 1) transfected cells. The ability of TLR14 to enhance LPS signalling suggests that TLR14 may be acting as a co-receptor for TLR4.

Example 2

Effect of siRNA Knockdown of TLR14 on LPS-mediated Signalling

In order to further confirm whether TLR14 functions as a co-receptor for TLR4, siRNAs specific for TLR14 knockdown were obtained from Qiagen. These TLR14 specific siRNAs were used to asses the effect of LPS induced IkB degradation and p38 phosphorylation.

siRNA for both TLR14 and a non-targeting negative control siRNA were transfected into U373s cells and knockdown of TLR14 was confirmed by western blotting. The resulting western blots confirming this knockdown are shown in FIG. 2(B) and FIG. 3.

LPS induced IkB degradation and p38 phosphorylation were used as readouts to assess the effect of reducing cellular levels of TLR14. Expression of β-Actin was used as a loading control (FIG. 2(A) and FIG. 3 respectively). FIG. 2(A) indicates that no LPS-induced IkB degradation was observed in the absence of TLR14. Similarly, LPS-induced p38 phosphorylation was severely impaired in cells treated with siRNA to TLR14 as shown in FIG. 3.

In order to ensure that these effects were not due to the non-specific knockdown of TLR4, the samples were also probed with a TLR4 antibody, this confirming that there is no evidence of TLR4 depletion from the cells that have been treated with siRNA to TLR14 (results not shown).

The results of examples 1 and 2 therefore clearly show that TLR14 enhances LPS induced cell signaling, while an absence of TLR14 abrogates normal responses to LPS. TLR14 is therefore for TLR4 function in response to binding of TLR4 with the PAMP, LPS.

Example 3

Determination of Binding of LPS to TLR14

An LPS binding assay was performed in order to determine LPS binding to TLR14. HEK293 cells were transfected with TLR14. After 24 hours, the cells were lysed and incubated with biotinylated LPS (1 μg/ml) or with unlabeled LPS for 1 hour at room temperature. A pull down assay was then performed on streptavidin agarose beads.

Analysis of the lysates by western blotting is shown in FIG. 4. Western blotting revealed that TLR14 was present in a complex with biotin-LPS. Inclusion of unlabeled LPS resulted in reduced binding as shown in FIG. 4 indicating that this interaction is specific. In FIG. 4(a), a 5-fold excess of unlabeled LPS has been included, whereas in FIG. 4(b), 25-fold and 50-fold excesses of unlabeled LPS has been included in the control samples.

Example 4

Effect of TLR14 siRNA Knockdown on IkB Degradation

THP1 cells were transfected with siRNA specific to TLR14 (Qiagen) using the amaxa based transfection system (program S-019).

After 72 hours, knockdown of TLR14 was confirmed by western blotting (FIG. 5(A)). A scrambled version of the Qiagen siRNA was used as a negative control to ensure that the siRNA was specific to TLR14. Cells were treated with 100 ng/ml LPS for the indicated time points and IkB degradation was measure by Western blotting (FIG. 5(B) and FIG. 5(C)).

siRNA mediated knockdown of TLR14 was therefore shown to marginally inhibit IkB degradation in response to stimulation with LPS.

Example 5

Effect of TLR14 Knockdown on IL-6 and TNF-α Cytokine Levels

THP1 cells were transfected with siRNA specific to TLR14 (Qiagen) using the amaxa based transfection system (program S-019). A scrambled version of Qiagen siRNA was used as a negative control to ensure that the siRNA was specific to TLR14. After 72 hours, the cells were stimulated with 100 ng/ml LPS for 24 hours. Supernatants were removed and IL-6 and TNF-a ELISA assays were performed, The results are shown in FIG. 6, with FIG. 6(A) shows the results of an ELISA which shows that knockdown of TLR14 causes a decrease in TNF-α production. FIG. 6(B) shows that TLR14 knockdown results in a reduction in IL-6 cytokine production.

Example 6

Expression and Localisation of TLR14 in the Membrane

U373 brain astocytoma cells were transfected with 4 ug of TLR14. After 2 hours, the cells were stimulated with 100 ng/ml LPS for 2 hours. The cells were fractionated into cytosol and membrane fractions. Western blot analysis confirms expression of TLR14 in the membrane.

FIG. 7 shows the resulting western blot. The cytosol fraction is shown on the left hand side, while the membrane fraction is shown on the right hand side. NT denotes a non-transfected cell, while T denotes a transfected cell. The results show that over expressed TLR14 is localized in the membrane.

Example 7

Expression of TLR14 in the Mouse Brain

Brains were removed from wild type (denoted WT) and experimental autoimmune encephalomyelitis (denoted EAE) mice, and dissected into the cortex, hippocampus and cerebellum. Western blot analysis of these sections confirms expression of TLR14 at the protein level.

FIG. 8 shows a western blot showing bands denoting the expression of TLR14 in the cortex (left hand side columns 1 and 2 of the gel), hippocampus (central columns 3 and 4), and cerebellum (right and columns 5 and 6).

It can be seen, particularly in relation to the EAE samples obtained from the cortex and hippocampus, that TLR14 expression levels are seen to be higher in these areas in EAE mice.

Example 8

Localisation of Endogenous TLR14 in THP1 Cells

THP-1 cells were seeded in 10 cm plates at $1\times10^5$ cells per ml overnight. After 24 hours, the medium was removed and the cells were washed with PBS before being scraped into fractionation buffer (10 mM Tris-HCl, 10 mM $MgCl_2$, 1 mM EDTA, 250 mM sucrose, 200 mM PMSF, pH 7.5). The samples were subjected to 20 strokes of a Dounce homogenizer and spun at 100,000×g for 1 hour. The supernatant (cytosolic fraction) was removed to a fresh tube and the pellet (membrane fraction) was resuspended in 50 μl of SDS-PAGE sample buffer [50 mM Tris Cl, pH 6.8/10% glycerol (vol/vol)/2% SDS (wt/vol)/0.1% bromophenol blue (wt/vol)/5% 2-mercaptoethanol]. Samples were analysed by SDS-PAGE and western blotting.

Membrane and cytosolic fractions of THP1 cells were prepared in order to determine the localisation of endogenous TLR14. The protein was isolated in the membrane fraction of these cells following ultracentrifugation, as shown in FIG. 9, wherein distinct banding can be seen in the gel column relating to the fraction derived from the membrane. Similar banding is absent from the cytosolic fraction. The results of this experiment therefore support the notion that TLR14 belongs to a family of membrane bound receptors.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention. Reference to any prior art in this specification is not, and should not be taken as, an acknowledgment or any form of suggestion that this prior art forms part of the common general knowledge in any country.

The invention claimed is:

1. A method for suppressing Toll-like Receptor 4 (TLR4))-mediated inflammation, the method comprising:
   administering, to a subject in need of suppression of TLR4-mediated inflammation, an inhibitory antibody against a Toll-like Receptor 14 (TLR14) protein, or an antigen binding fragment thereof, said TLR14 protein comprising the amino acid sequence of SEQ ID NO: 1, wherein the antibody or antigen binding fragment thereof:
   (i) belongs to a subclass chosen from IgG1, IgG2a, IgG2b, IgG3, or IgG4; and
   (ii) is administered in an amount sufficient to suppress TLR4-mediated inflammation.

2. The method as claimed in claim 1, wherein the antibody or antigen binding fragment thereof inhibits activation of NF-KB, interferon regulated factor 3, mitogen-activated protein kinase (MAPK), p38, c-jun N-terminal kinase (JNK) or p42/44.

3. The method of claim 1, wherein the antibody, or antigen binding fragment thereof, is a chimeric, CDR-grafted, humanized or chimeric antibody.

4. The method of claim 1, wherein the antigen binding fragment thereof is an Fab, an F(ab')2, an fv or a scFv.

5. The method of claim 1, wherein the subject is a human.

6. A method for the treatment of septicaemia or septic shock, the method comprising:
   administering, to a subject in need thereof, an antibody against a Toll-like Receptor 14 (TLR14) protein, or an antigen binding fragment thereof, said TLR14 protein comprising the amino acid sequence of SEQ ID NO:1, wherein the antibody or antigen binding fragment thereof is administered in an amount sufficient to treat the septicaemia or septic shock, and
   wherein the antibody belongs to a subclass chosen from IgG1, IgG2a, IgG2b, IgG3, or IgG4.

7. The method as claimed in claim 6, further comprising the step of administering to the subject a composition which inhibits the expression or biological function of CD14, wherein the composition is chosen from a CD14 inhibitory nucleic acid, a soluble form of CD14, a peptide CD14 inhibitor compound, a CD14 fusion protein, or an antibody against CD14.

8. The method as claimed in claim 6, wherein the antibody or antigen binding fragment thereof inhibits an association of Toll-like Receptor 14 with Toll-like Receptor 4.

9. The method of claim 6, wherein the antibody, or antigen binding fragment thereof, is a chimeric, CDR-grafted, humanized or chimeric antibody.

10. A method for suppressing Toll-like Receptor 4 (TLR4)-mediated inflammatory activation and signaling, the method comprising:
    contacting a cell expressing a Toll-like Receptor 14 (TLR14) protein and a TLR4 protein with an antibody against the TLR14 protein, or an antigen binding fragment thereof, wherein the antibody or antigen binding fragment thereof:
    (i) belongs to a subclass chosen from IgG1, IgG2a, IgG2b, IgG3, or IgG4, and
    (ii) is in an amount sufficient to inhibit a biological function of TLR14, and
    wherein the biological function of TLR14 results in the TLR4-mediated inflammatory activation and signaling, thereby suppressing TLR4-mediated inflammatory activation and signaling.

11. The method of claim 10, wherein the antibody or antigen binding fragment thereof inhibits an association of TLR14 with TLR4.

12. The method of claim 10, wherein the TLR14 protein comprises the amino acid sequence of SEQ ID NO:1.

13. The method of claim 10, wherein the antibody, or antigen binding fragment thereof, is a chimeric, CDR-grafted, humanized or chimeric antibody.

14. The method of claim 10, wherein the antigen binding fragment thereof is an Fab, an F(ab')2, an Fv or a scFv.

15. The method of claim 10, wherein the contacting step occurs in vitro.

* * * * *